US010537395B2

(12) United States Patent
Perez

(10) Patent No.: US 10,537,395 B2
(45) Date of Patent: Jan. 21, 2020

(54) NAVIGATION TRACKER WITH KINEMATIC CONNECTOR ASSEMBLY

(71) Applicant: MAKO Surgical Corp., Ft. Lauderdale, FL (US)

(72) Inventor: Timothy Wade Perez, Plantation, FL (US)

(73) Assignee: MAKO Surgical Group, Ft. Lauderdale, FL (US)

( * ) Notice: Subject to any disclaimer, the term of this patent is extended or adjusted under 35 U.S.C. 154(b) by 220 days.

(21) Appl. No.: 15/601,127

(22) Filed: May 22, 2017

(65) Prior Publication Data
US 2017/0340395 A1  Nov. 30, 2017

Related U.S. Application Data

(60) Provisional application No. 62/341,886, filed on May 26, 2016.

(51) Int. Cl.
*A61B 17/00* (2006.01)
*A61B 34/20* (2016.01)
(Continued)

(52) U.S. Cl.
CPC .............. *A61B 34/20* (2016.02); *A61B 34/30* (2016.02); *A61B 2034/2055* (2016.02); *A61B 2034/302* (2016.02); *A61B 2090/3983* (2016.02)

(58) Field of Classification Search
CPC .... A61B 2090/3983; A61B 2034/2055; A61B 34/20; Y10T 403/585; Y10T 403/583; Y10T 403/581; Y10T 403/58
See application file for complete search history.

(56) References Cited

U.S. PATENT DOCUMENTS 4,362,416 A * 12/1982 Kaimo ................... E02D 5/523
                                                                 403/316
5,017,139 A    5/1991 Mushabac
(Continued)

FOREIGN PATENT DOCUMENTS

DE        10335388 B4    6/2006
EP         1873666 A1    1/2008
(Continued)

OTHER PUBLICATIONS

English language abstract and machine-assisted English translation for DE 103 35 388 extracted from espacenet.com database on Oct. 11, 2017, 14 pages.
(Continued)

*Primary Examiner* — Zade Coley
*Assistant Examiner* — Amy R Sipp
(74) *Attorney, Agent, or Firm* — Howard & Howard Attorneys PLLC

(57) ABSTRACT

A kinematic connector assembly for kinematically coupling two objects is provided. The kinematic connector assembly comprises a receiver defining a cavity and having a plurality of constraint surfaces accessible in the cavity. The kinematic connector assembly further comprises a key having a triplicity of kinematic elements to repeatably position the key in the receiver. The kinematic connector assembly further comprises a preloading mechanism having a load member movable between a clamped position and an unclamped position to secure the key in the receiver, so that the kinematic elements contact the receiver at the plurality of constraint surfaces such that the key is kinematically constrained to the receiver by being constrained by six points of contact with the receiver.

34 Claims, 21 Drawing Sheets

(51) Int. Cl.
*A61B 34/30* (2016.01)
*A61B 90/00* (2016.01)

(56) References Cited

U.S. PATENT DOCUMENTS

| | | | |
|---|---|---|---|
| 5,142,930 A | 9/1992 | Allen et al. |
| 5,167,464 A | 12/1992 | Voellmer |
| 5,174,772 A | 12/1992 | Vranish |
| 5,566,681 A | 10/1996 | Manwaring et al. |
| 5,676,673 A | 10/1997 | Ferre et al. |
| 5,683,118 A | 11/1997 | Slocum |
| 5,748,827 A | 5/1998 | Holl et al. |
| 5,855,582 A | 1/1999 | Gildenberg |
| 5,987,960 A | 11/1999 | Messner et al. |
| 6,021,343 A | 2/2000 | Foley et al. |
| 6,052,611 A | 4/2000 | Yanof et al. |
| 6,066,141 A | 5/2000 | Dall et al. |
| 6,167,145 A | 12/2000 | Foley et al. |
| 6,190,395 B1 | 2/2001 | Williams |
| 6,193,430 B1 | 2/2001 | Culpepper et al. |
| 6,203,543 B1 | 3/2001 | Glossop |
| 6,226,548 B1 | 5/2001 | Foley et al. |
| 6,377,011 B1 | 4/2002 | Ben-Ur |
| 6,379,071 B1 | 4/2002 | Sorvino |
| 6,434,507 B1 | 8/2002 | Clayton et al. |
| 6,484,049 B1 | 11/2002 | Seeley et al. |
| 6,514,259 B2 | 2/2003 | Picard et al. |
| 6,517,484 B1 | 2/2003 | Wilk et al. |
| 6,529,765 B1 | 3/2003 | Franck et al. |
| 6,572,624 B2 | 6/2003 | U et al. |
| 6,719,757 B2 | 4/2004 | Neubauer et al. |
| 6,729,589 B2 | 5/2004 | Shelef |
| 6,738,657 B1 | 5/2004 | Franklin et al. |
| 6,746,172 B2 | 6/2004 | Culpepper |
| 6,856,828 B2 | 2/2005 | Cossette et al. |
| 6,893,447 B2 | 5/2005 | Dominguez et al. |
| 6,932,823 B2 | 8/2005 | Grimm et al. |
| 7,043,961 B2 | 5/2006 | Pandey et al. |
| 7,153,297 B2 | 12/2006 | Peterson |
| 7,153,308 B2 | 12/2006 | Peterson |
| 7,166,114 B2 | 1/2007 | Moctezuma De La Barrera et al. |
| 7,274,958 B2 | 9/2007 | Jutras et al. |
| 7,300,432 B2 | 11/2007 | Surma et al. |
| 7,302,288 B1 | 11/2007 | Schellenberg |
| 7,314,048 B2 | 1/2008 | Couture et al. |
| 7,366,561 B2 | 4/2008 | Mills et al. |
| 7,377,924 B2 | 5/2008 | Raistrick et al. |
| 7,419,492 B2 | 9/2008 | Yoon et al. |
| 7,458,977 B2 | 12/2008 | McGinley et al. |
| 7,477,926 B2 | 1/2009 | McCombs |
| 7,547,307 B2 | 6/2009 | Carson et al. |
| 7,558,617 B2 | 7/2009 | Vilsmeier |
| 7,641,660 B2 | 1/2010 | Lakin et al. |
| 7,646,899 B2 | 1/2010 | Fitzpatrick |
| 7,668,584 B2 | 2/2010 | Jansen |
| 7,688,998 B2 | 3/2010 | Tuma et al. |
| 7,725,182 B2 | 5/2010 | Sutardja |
| 7,726,564 B2 | 6/2010 | Goldbach |
| 7,736,368 B2 | 6/2010 | Couture et al. |
| 7,753,910 B2 | 7/2010 | Ritland |
| 7,764,985 B2 | 7/2010 | McCombs et al. |
| 7,771,436 B2 | 8/2010 | Moctezuma De La Barrera et al. |
| 7,776,000 B2 | 8/2010 | Schaffrath et al. |
| 7,780,681 B2 | 8/2010 | Sarin et al. |
| 7,794,469 B2 | 9/2010 | Kao et al. |
| 7,881,770 B2 | 2/2011 | Melkent et al. |
| 7,925,328 B2 | 4/2011 | Urquhart et al. |
| 7,970,174 B2 | 6/2011 | Goldbach |
| 7,970,190 B2 | 6/2011 | Steinle et al. |
| 7,993,353 B2 | 8/2011 | Roßner et al. |
| 8,021,369 B2 | 9/2011 | Curry |
| 8,066,961 B2 | 11/2011 | Costello, III et al. |
| 8,105,339 B2 | 1/2012 | Melkent et al. |
| 8,109,877 B2 | 2/2012 | Moctezuma de la Barrera et al. |
| 8,114,134 B2 | 2/2012 | Winslow et al. |
| 8,152,726 B2 | 4/2012 | Amiot et al. |
| 8,165,658 B2 | 4/2012 | Waynik et al. |
| 8,202,322 B2 | 6/2012 | Doty |
| 8,226,724 B2 | 7/2012 | Doty |
| 8,277,505 B1 | 10/2012 | Doty |
| 8,348,954 B2 | 1/2013 | Carls et al. |
| 8,357,165 B2 | 1/2013 | Grant et al. |
| 8,382,766 B2 | 2/2013 | Warkentine et al. |
| 8,386,022 B2 | 2/2013 | Jutras et al. |
| 8,457,719 B2 | 6/2013 | Moctezuma de la Barrera et al. |
| 8,460,277 B2 | 6/2013 | Suarez et al. |
| 8,469,965 B2 | 6/2013 | Neubauer et al. |
| 8,512,346 B2 | 8/2013 | Couture |
| 8,535,329 B2 | 9/2013 | Sarin et al. |
| 8,549,732 B2 | 10/2013 | Burg et al. |
| 8,611,985 B2 | 12/2013 | Lavallee et al. |
| 8,644,570 B2 | 2/2014 | Hartmann et al. |
| 8,657,809 B2 | 2/2014 | Schoepp |
| 8,672,490 B2 | 3/2014 | Shafer et al. |
| 8,709,017 B2 | 4/2014 | Plaßky et al. |
| 8,721,660 B2 | 5/2014 | Ulfarsson et al. |
| 8,747,419 B2 | 6/2014 | Solar et al. |
| 8,800,939 B2 | 8/2014 | Karsak et al. |
| 8,845,655 B2 | 9/2014 | Henderson et al. |
| 8,862,200 B2 | 10/2014 | Sherman et al. |
| 8,942,788 B2 | 1/2015 | Roger |
| 8,945,132 B2 | 2/2015 | Plaßy et al. |
| 9,066,751 B2 | 6/2015 | Sasso |
| 9,082,319 B2 | 7/2015 | Shimada et al. |
| 9,085,401 B2 | 7/2015 | Shafer et al. |
| 9,095,376 B2 | 8/2015 | Plaßky et al. |
| 9,125,624 B2 | 9/2015 | Dekel et al. |
| 9,131,987 B2 | 9/2015 | Stefanchik et al. |
| 9,157,698 B2 | 10/2015 | Cosentino |
| 9,161,799 B2 | 10/2015 | Benson et al. |
| 9,495,509 B2 | 11/2016 | Amiot et al. |
| 2003/0086748 A1* | 5/2003 | Culpepper ............... F16M 7/00 403/13 |
| 2003/0135213 A1 | 7/2003 | LeHuec et al. |
| 2004/0068263 A1 | 4/2004 | Chouinard et al. |
| 2004/0127902 A1 | 7/2004 | Suzuki et al. |
| 2004/0171930 A1 | 9/2004 | Grimm et al. |
| 2005/0049485 A1 | 3/2005 | Harmon et al. |
| 2005/0109855 A1 | 5/2005 | McCombs |
| 2005/0124988 A1 | 6/2005 | Terrill-Grisoni et al. |
| 2005/0137599 A1 | 6/2005 | Masini |
| 2005/0187562 A1 | 8/2005 | Grimm et al. |
| 2005/0203528 A1 | 9/2005 | Couture et al. |
| 2005/0228387 A1 | 10/2005 | Paul |
| 2005/0277933 A1 | 12/2005 | Wall et al. |
| 2006/0015018 A1 | 1/2006 | Jutras et al. |
| 2006/0015119 A1 | 1/2006 | Plassky et al. |
| 2006/0052691 A1 | 3/2006 | Hall et al. |
| 2006/0052792 A1 | 3/2006 | Boettiger et al. |
| 2006/0142656 A1 | 6/2006 | Malackowski et al. |
| 2006/0161059 A1 | 7/2006 | Wilson |
| 2006/0195111 A1 | 8/2006 | Couture |
| 2006/0235290 A1 | 10/2006 | Gabriel et al. |
| 2006/0241405 A1 | 10/2006 | Leitner et al. |
| 2007/0233156 A1 | 10/2007 | Metzger |
| 2008/0027452 A1 | 1/2008 | Sheffer et al. |
| 2008/0114375 A1 | 5/2008 | von Jako |
| 2008/0183108 A1 | 7/2008 | Huber et al. |
| 2009/0024127 A1 | 1/2009 | Lechner et al. |
| 2009/0099445 A1 | 4/2009 | Burger |
| 2009/0118742 A1 | 5/2009 | Hartmann et al. |
| 2009/0163930 A1 | 6/2009 | Aoude et al. |
| 2009/0247863 A1 | 10/2009 | Proulx |
| 2009/0270928 A1 | 10/2009 | Stone et al. |
| 2009/0281417 A1 | 11/2009 | Hartmann et al. |
| 2009/0281421 A1 | 11/2009 | Culp et al. |
| 2009/0306499 A1 | 12/2009 | Van Vorhis et al. |
| 2010/0023062 A1 | 1/2010 | Faillace et al. |
| 2010/0063511 A1 | 3/2010 | Plassky et al. |
| 2010/0094358 A1 | 4/2010 | Moore et al. |
| 2010/0125286 A1 | 5/2010 | Wang et al. |
| 2010/0160932 A1 | 6/2010 | Gschwandtner et al. |
| 2010/0192961 A1 | 8/2010 | Amiot et al. |
| 2011/0004259 A1 | 1/2011 | Stallings et al. |

(56) References Cited

U.S. PATENT DOCUMENTS

| | | |
|---|---|---|
| 2011/0098553 A1 | 4/2011 | Robbins et al. |
| 2011/0160572 A1 | 6/2011 | McIntosh |
| 2011/0166446 A1 | 7/2011 | Whitmore, III et al. |
| 2012/0016427 A1 | 1/2012 | Stindel et al. |
| 2012/0109228 A1 | 5/2012 | Boyer et al. |
| 2012/0143048 A1 | 6/2012 | Finlay |
| 2013/0053895 A1 | 2/2013 | Stoll et al. |
| 2013/0096573 A1 | 4/2013 | Kang et al. |
| 2013/0123580 A1 | 5/2013 | Peters et al. |
| 2013/0165947 A1 | 6/2013 | Nguyen et al. |
| 2013/0261783 A1 | 10/2013 | Daon et al. |
| 2013/0331686 A1 | 12/2013 | Freysinger et al. |
| 2014/0049629 A1 | 2/2014 | Siewerdsen et al. |
| 2014/0200621 A1* | 7/2014 | Malackowski ........ A61B 34/30 606/86 R |
| 2014/0236159 A1 | 8/2014 | Haider et al. |
| 2014/0276943 A1 | 9/2014 | Bowling et al. |
| 2014/0364858 A1 | 12/2014 | Li et al. |
| 2015/0031982 A1 | 1/2015 | Piferi et al. |
| 2015/0088108 A1 | 3/2015 | Tyc et al. |
| 2015/0173911 A1 | 6/2015 | Doty |
| 2015/0182285 A1 | 7/2015 | Yen et al. |
| 2015/0182293 A1 | 7/2015 | Yang et al. |
| 2015/0209119 A1 | 7/2015 | Theodore et al. |
| 2015/0257851 A1 | 9/2015 | Plassky et al. |
| 2015/0265769 A1 | 9/2015 | Bratbak et al. |
| 2015/0282735 A1 | 10/2015 | Rossner |
| 2015/0309187 A1 | 10/2015 | Shafer et al. |
| 2016/0249988 A1 | 9/2016 | Pfeifer et al. |
| 2017/0333136 A1 | 11/2017 | Hladio et al. |

FOREIGN PATENT DOCUMENTS

| | | | |
|---|---|---|---|
| JP | 2008538184 A | | 10/2008 |
| JP | 2011515163 A | | 5/2011 |
| WO | 02080773 A1 | | 10/2002 |
| WO | 2006091494 A1 | | 8/2006 |
| WO | 2007014470 A2 | | 2/2007 |
| WO | 2007038135 A2 | | 4/2007 |
| WO | 2008104548 A1 | | 9/2008 |
| WO | 2008113008 A2 | | 9/2008 |
| WO | 2008133615 A1 | | 11/2008 |
| WO | 2009117832 A1 | | 10/2009 |
| WO | 2010055193 A1 | | 5/2010 |
| WO | 2012103407 A1 | | 8/2012 |
| WO | 2012127353 A1 | | 9/2012 |
| WO | 2013091112 A1 | | 6/2013 |
| WO | 2013177334 A1 | | 11/2013 |
| WO | 2014091053 A1 | | 6/2014 |
| WO | 2014139022 A1 | | 9/2014 |
| WO | 2014198784 A1 | | 12/2014 |
| WO | 2015013518 A1 | | 1/2015 |
| WO | 2015067743 A2 | | 5/2015 |
| WO | 2015090434 A1 | | 6/2015 |
| WO | 2015150877 A1 | | 10/2015 |

OTHER PUBLICATIONS

English language abstract and machine-assisted English translation for WO 2008/104548 extracted from espacenet.com database on Oct. 12, 2017, 20 pages.

English language abstract for WO 2014/091053 and machine-assisted English translation for equivalent ES 2477140 of WO 2014/091053 extracted from espacenet.com database on Oct. 26, 2017, 10 pages.

English language abstract for WO 2015/067743 extracted from espacenet.com database on Oct. 12, 2017, 2 pages.

English language abstract for JP 2008-538184 extracted from espacenet.com database on Jun. 18, 2018, 2 pages.

English language abstract for JP 2011-515163 extracted from espacenet.com database on Jun. 18, 2018, 2 pages.

English language abstract for EP 1 873 666 A1 extracted from the www.espacenet.com database on Dec. 12, 2018.

* cited by examiner

NAVIGATION TRACKER WITH KINEMATIC CONNECTOR ASSEMBLY

RELATED APPLICATION

This application claims priority to and the benefit of U.S. Provisional Patent Application No. 62/341,886, filed on May 26, 2016, the entire content of which is hereby incorporated by reference herein.

TECHNICAL FIELD

The present disclosure generally relates to a kinematic connector assembly.

BACKGROUND

Navigation systems assist users in locating objects. For instance, navigation systems are used in industrial, aerospace, and medical applications. In the medical field, navigation systems assist surgeons in locating surgical instruments and anatomy for the purpose of accurately placing the surgical instruments relative to the anatomy.

Navigation systems may employ light signals, sound waves, magnetic fields, radio frequency signals, etc. in order to track the position and/or orientation of objects. Often the navigation system includes tracking devices attached to the objects being tracked. A localizer cooperates with tracking elements on the tracking devices to determine positions of the tracking elements, and ultimately to determine a position and orientation of the objects. The navigation system monitors movement of the objects via the tracking devices. Often, there is a need for the tracking devices to be releasably attached to the objects. However, when the tracking device is removed from the object and then reattached, its positional relationship with respect to the object usually changes, requiring recalibration or re-registration of the tracking device to the object.

As a result, there is a need in the art for tracking devices that overcome one or more of the problems mentioned above.

SUMMARY

A kinematic connector assembly comprises a receiver defining a cavity with a plurality of constraint surfaces accessible in the cavity and a key having a triplicity of kinematic elements to repeatably position the key in the receiver. The kinematic connector assembly further comprises a preloading mechanism with a load member. The load member is movable between a clamped position and an unclamped position to secure the key in the receiver, such that the kinematic elements contact the receiver at the plurality of constraint surfaces to kinematically constrain the key to the receiver by being constrained by six points of contact with the receiver.

A tracker assembly to track an object comprises a tracker head, and a kinematic connector attached to the tracker head. The kinematic connector comprises one of a receiver or key with the other of the receiver or key being coupled to the object to be tracked.

BRIEF DESCRIPTION OF THE DRAWINGS

Advantages of the present disclosure will be readily appreciated as the same becomes better understood by reference to the following detailed description when considered in connection with the accompanying drawings wherein.

DETAILED DESCRIPTION

Figure 1:
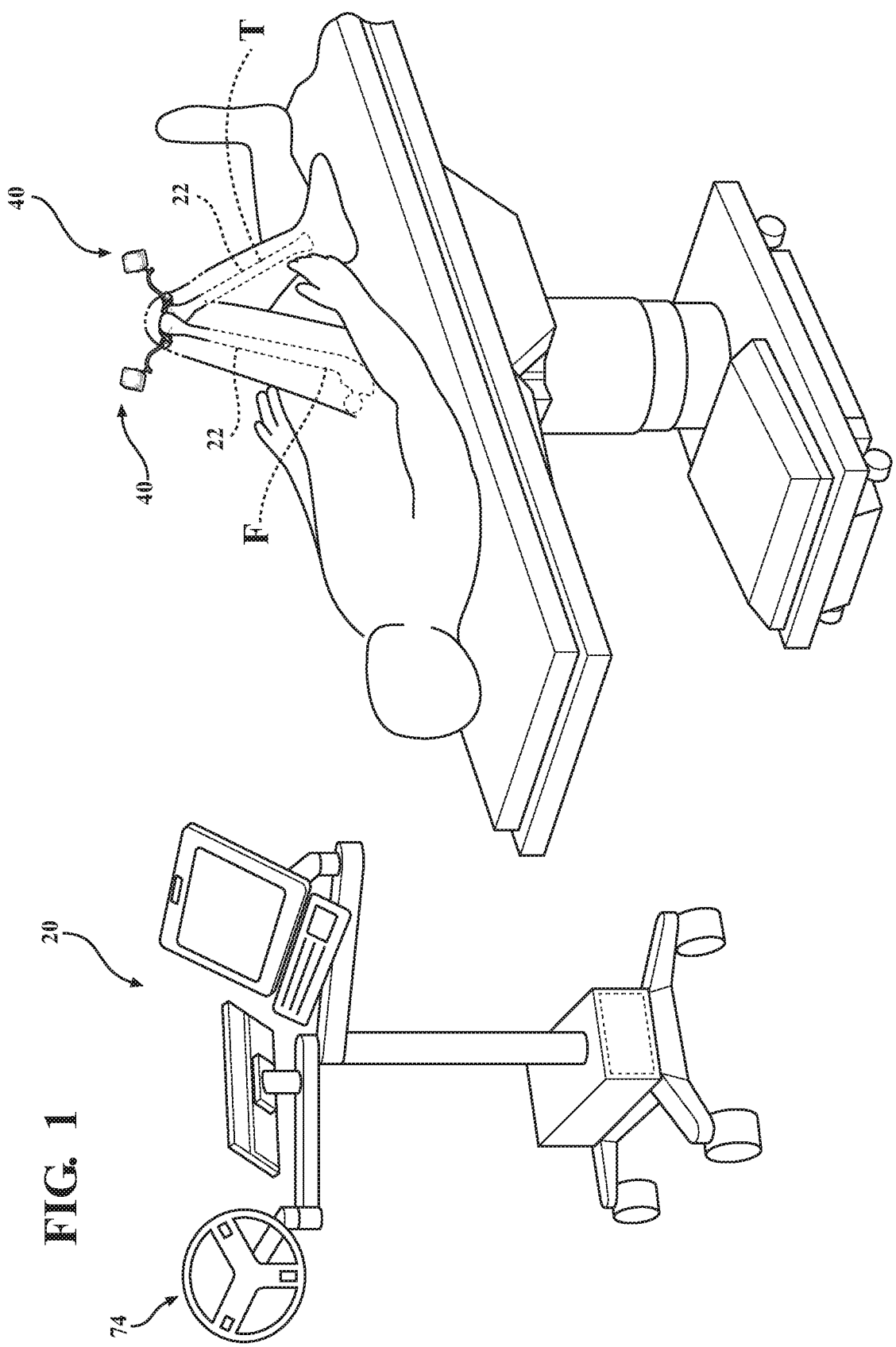
FIG. 1 is a perspective view of a surgical navigation system and two tracker assemblies being used in conjunction with a patient.

Referring to FIG. 1 a navigation system 20 is illustrated. The navigation system 20 is shown in a surgical setting such as an operating room of a medical facility. The navigation system 20 is set up to track movement of various objects in the operating room. Such objects may include, for example, a patient's bones 22, such as a femur F of the patient, and a tibia T of the patient. The navigation system 20 tracks these objects for purposes of displaying their relative positions and orientations to the surgeon and, in some cases, for purposes of controlling or constraining movement of a surgical instrument relative to a predefined path or anatomical boundary. The navigation system 20 includes at least one tracker assembly 40 firmly affixed to the object that is to be tracked.

The navigation system 20 further includes a localizer 74, which communicates with the navigation system 20. In the embodiment shown, the localizer 74 is an optical localizer and includes optical sensors, such as a camera unit.

Figure 2:
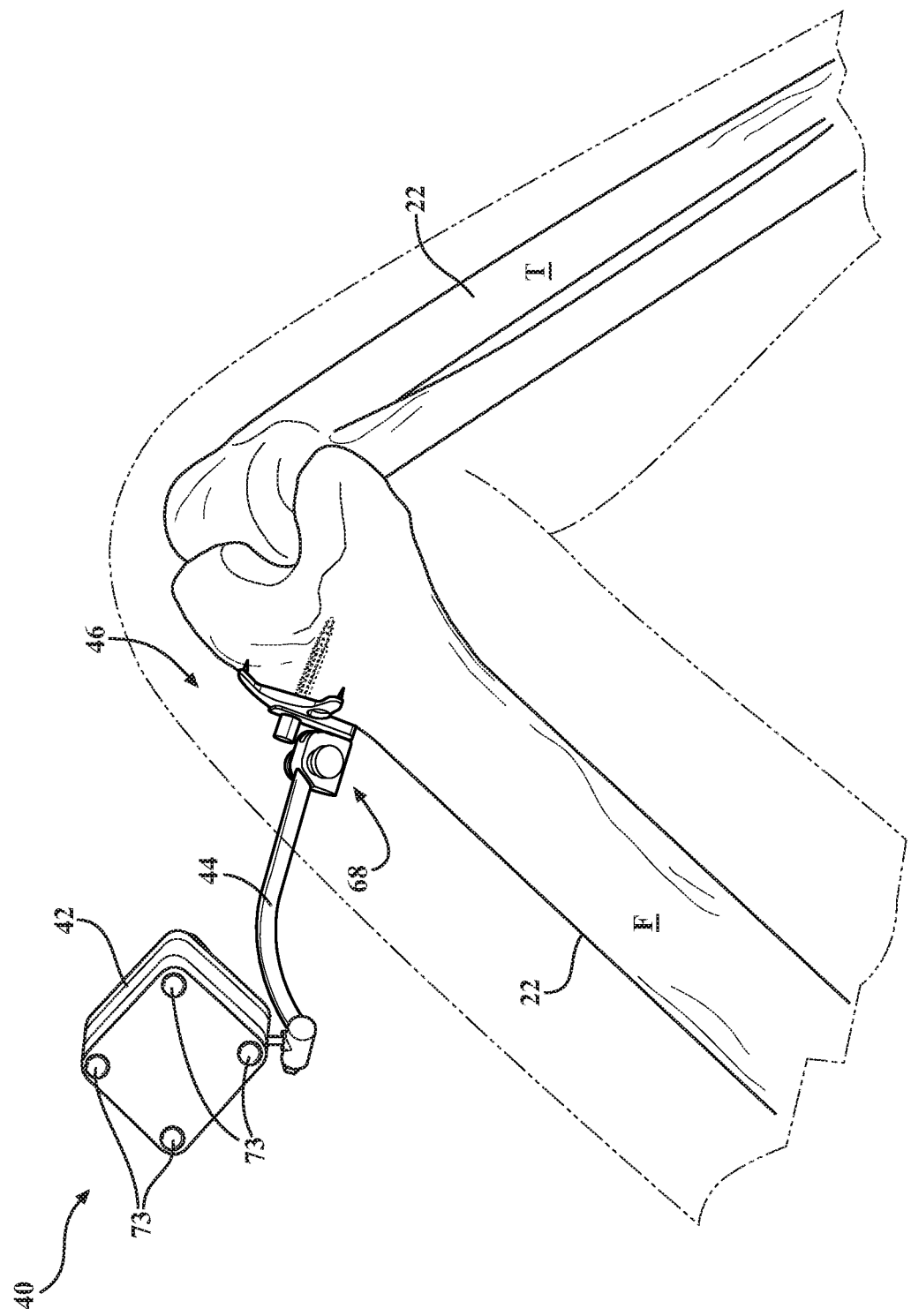
FIG. 2 is an enlarged perspective view of one of the tracker assemblies of FIG. 1 being used in conjunction with the patient.

Referring to FIG. 2, the tracker assembly 40 comprises a tracker head 42, an extension arm 44, and a bone plate 68. During use the tracker assembly 40 is firmly affixed to an object to be tracked, such as sections of bone 22. In FIG. 2, one tracker assembly 40 is shown firmly affixed to the femur F of the patient.

Each tracker head 42 has a plurality of tracking elements 73 for emitting light to the localizer 74. More specifically, each tracker head 42 has at least three, and preferably four, active tracking elements 73 for transmitting light signals to the optical sensors. The active tracking elements 73 can be, for example, light emitting diodes (LEDs) transmitting light signals, such as infrared light. In some embodiments, the light signals from the LEDs are fired at different frequencies for each tracker assembly 40. Each of the LEDs may be connected to a tracker controller (not shown) of the associated tracker assembly 40.

The tracker assemblies 40 may be active trackers or passive trackers. The tracker assemblies 40 may also be trackers for electro-magnetic navigation systems, ultrasound navigation systems, and the like. Other types of navigation systems in which the tracker assembly 40 is used are contemplated.

During a surgical procedure a need may arise to remove a tracker head 42 from the object to be tracked. The tracker head 42 may block the surgeon from accessing a particular area of the surgical site, or hinder the procedure in other ways. Once the tracker head 42 is disconnected from the object to be tracked, the position of the tracked object is unknown until the tracker head 42 is reconnected. When the tracker head 42 is reconnected the surgical navigation system 20 will resume tracking the object. As such, the tracker head 42 must be reconnected in the same position relative to the object in order to properly track the object.

Figure 3:
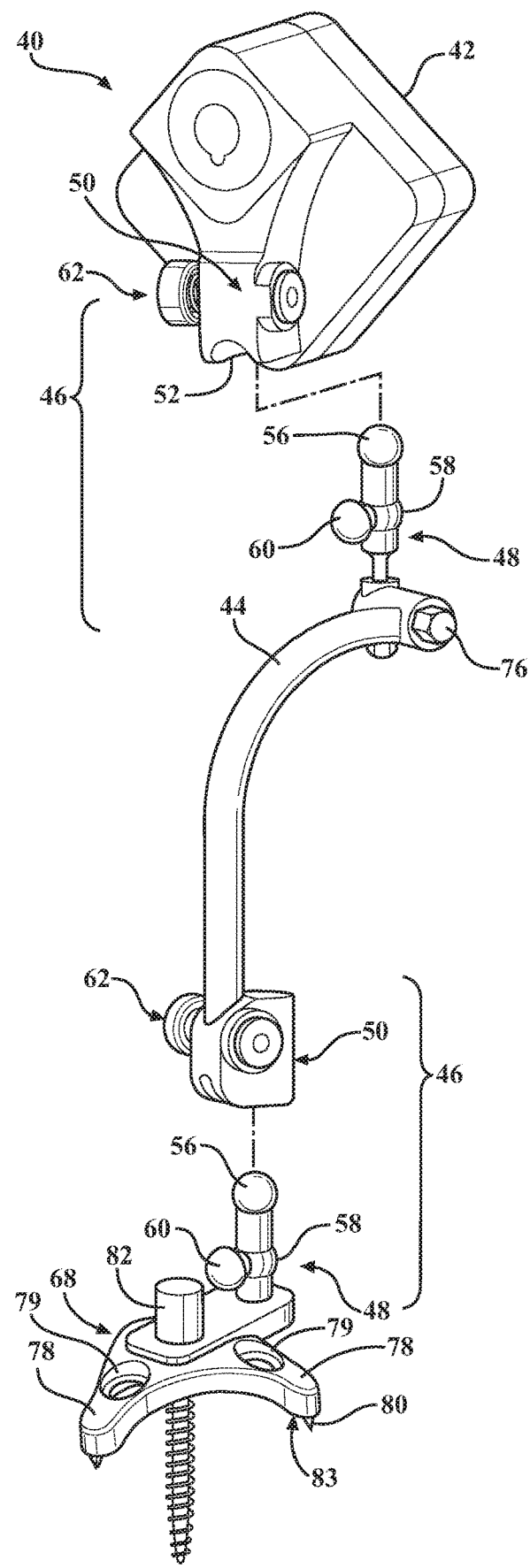
FIG. 3 is an exploded view of one embodiment of a tracker assembly.
Figure 3A:
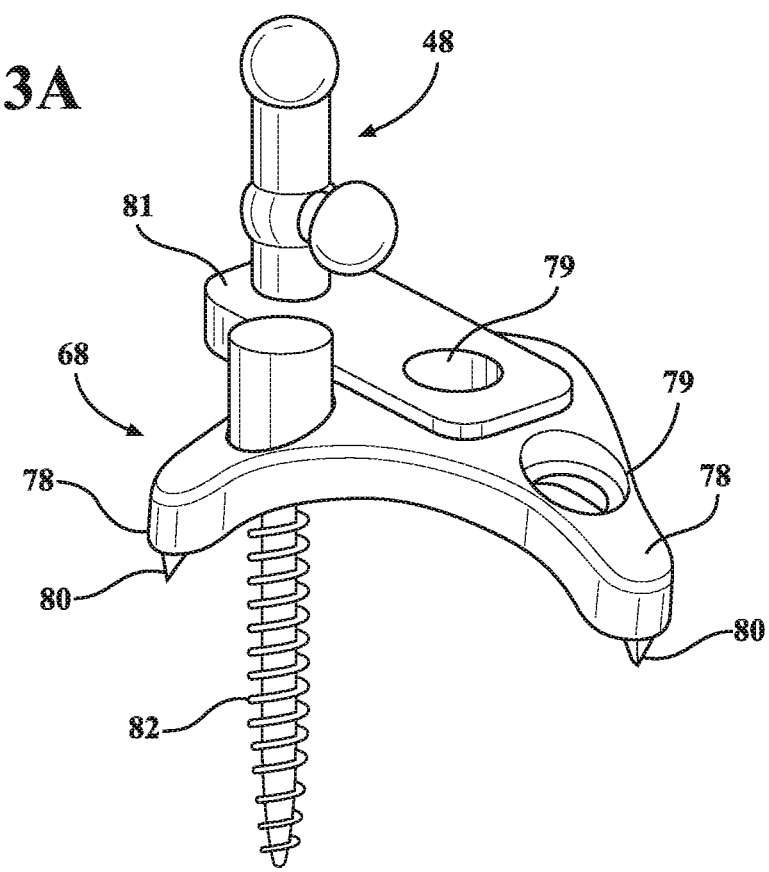
FIG. 3A is a perspective view of a bone plate and a bone screw.
Figure 3B:
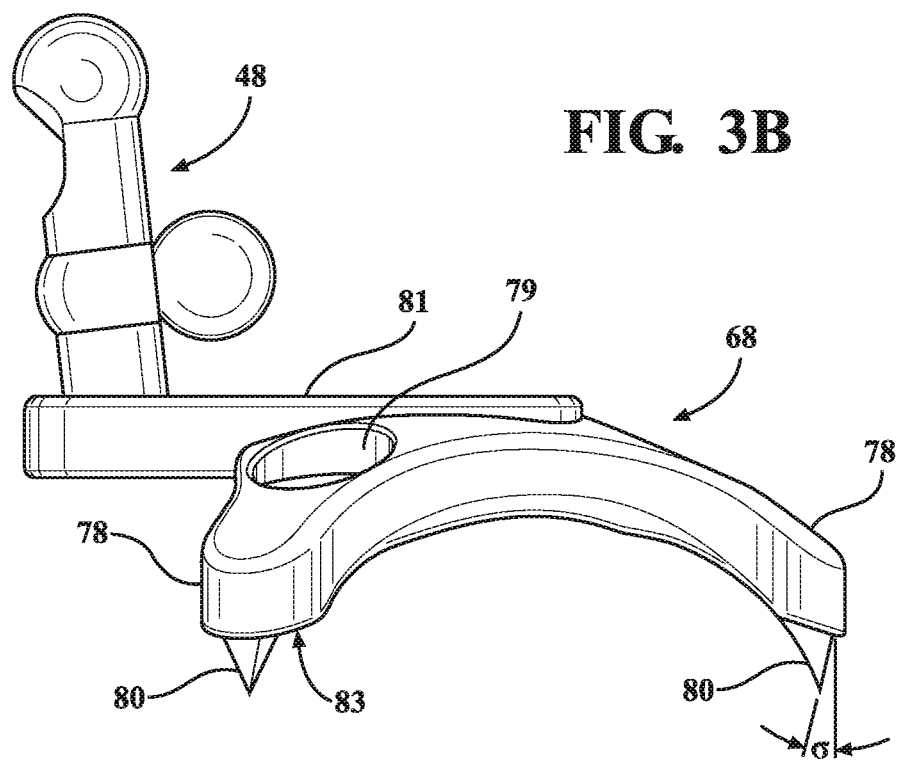
FIG. 3B is an elevational view of the bone plate of FIG. 3A.
Figure 3C:
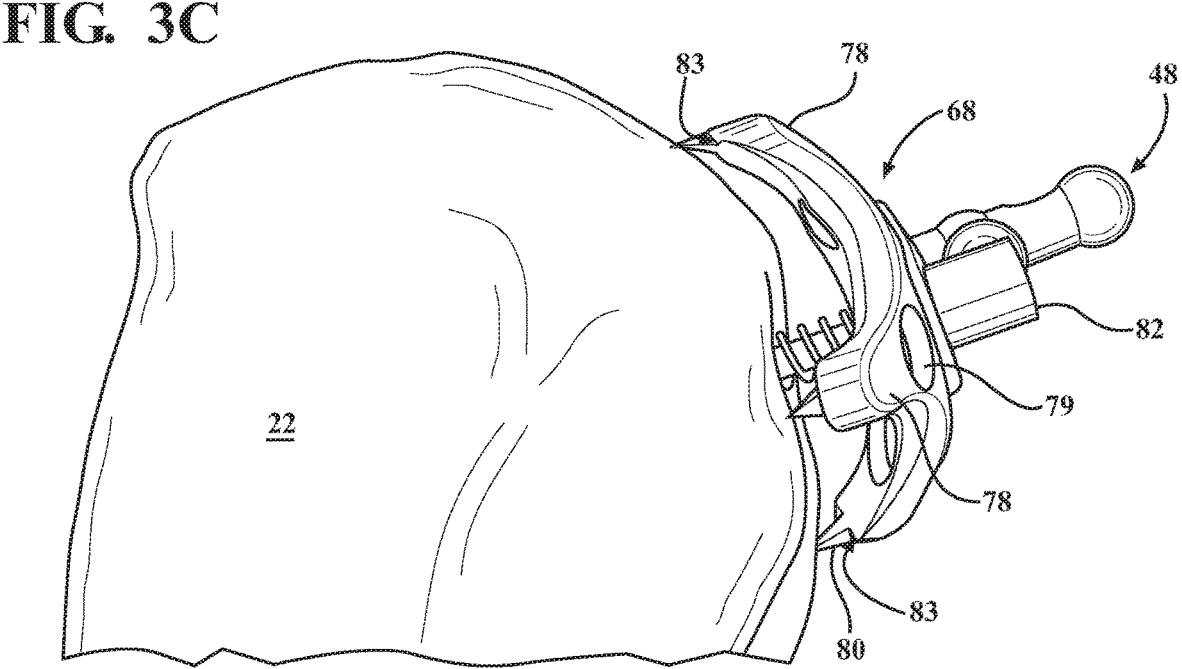
FIG. 3C is a perspective view of the bone plate being prepared to be secured in bone.
Figure 3D:
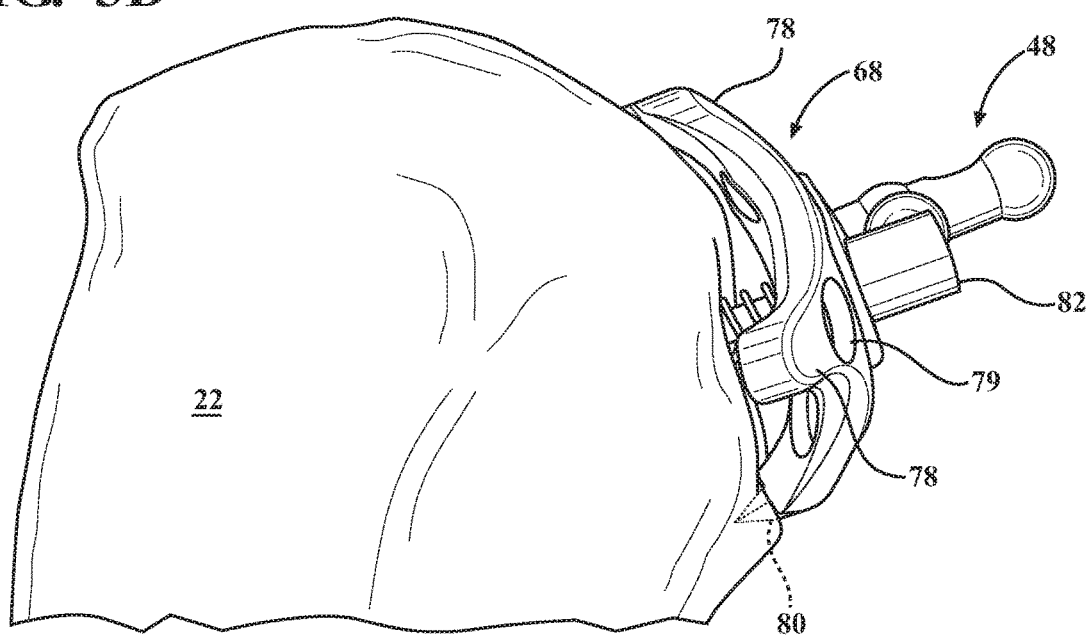
FIG. 3D is a perspective view of the bone plate secured in bone.

Referring to FIG. 3, a kinematic connector assembly 46 is used to couple the tracker head 42 to the extension arm 44 in the same relative position throughout the surgical procedure. The kinematic connector assembly 46 allows the tracker head 42 to be disconnected from and repeatably connected to either the extension arm 44 or the bone plate 68 without requiring the navigation system 20 to be recalibrated and/or the tracker assembly 40 to be re-registered to the object. Likewise, the tracker head 42 and the extension arm 44 could be disconnected from and repeatably connected to the bone plate 68 as a unit without requiring the navigation system 20 to be recalibrated or the tracker assembly 40 to be re-registered to the object. At least one kinematic connector assembly 46 is used to couple the tracker head 42 and the bone plate 68 to opposite ends of the extension arm 44.

In the embodiment shown, the tracker head 42 is coupled to a first end of the extension arm 44 using a first kinematic connector assembly 46. The bone plate 68 is coupled to a second end of the extension arm 44 through a second kinematic connector assembly 46. It should be appreciated that the second kinematic connector assembly 46 is generally the same as the first kinematic connector assembly 46 such that components from the first kinematic connector assembly 46 are interchangeable with components from the second kinematic connector assembly 46. For example, the tracker head 42 may be coupled directly to the bone plate 68 such that the tracker assembly 40 only comprises one kinematic connector assembly 46.

The kinematic connector assembly 46 may be made from a surgical grade stainless steel however, other metals, polymers, ceramics, and any combination thereof may be utilized.

The extension arm 44 is an elongate rod with a first end and a second end. The extension arm 44 locates the tracker head 42 away from the object that is to be tracked. The extension arm 44 is shown as a curved rod with a circular cross section. The extension arm 44 may be of any suitable length with more or fewer distinct curves that each may be curved greater or less than shown such that the extension arm 44 avoids any obstructions between the first and second ends. The curves may be suitable to place the tracker head 42 away from a surgical site of interest so that the tracker head 42 remains out of the way of the surgical site. For example, the extension arm 44 may be U-shaped, C-shaped, S-shaped, or straight. The rod may be any suitable cross section shape such as round, square, or hexagonal.

The first end of the extension arm 44 includes an adjustable mount 76 which allows the surgeon to aim the tracker head 42 prior to the surgical procedure.

The bone plate 68 is used to firmly affix the tracker assembly 40 to a bone during a surgical procedure. The bone plate 68 comprises three arms 78 each having at least one claw 80 to pierce the bone 22 and position the bone plate 68. The bone plate 68 may further include a screw 82. The screw 82 is disposed in an aperture 79 extending through the bone plate 68 and is engageable with a bone 22. The screw 82 is threaded into the bone 22 and draws the claws 80 of the bone plate 68 into engagement with the bone 22. Each of the claws 80 extend from a bone pad surface 83 of the arms 78. The screw 82 may be placed in alternative apertures 79 of the bone plate 68 or multiple screws 82 may be employed in multiple apertures 79 to secure the bone plate 68.

The bone plate 68 has top and bottom surfaces with a peripheral side surface extending therebetween. The bottom surface is generally concavely shaped between the claws 80. The bottom surface forms an obtuse angle with the bone pad surfaces 83 in the embodiments shown such that the bone pad surfaces 83 are generally disposed in planes that are more parallel to the bone being penetrated than the bottom surface of the bone plate 68. The claws 80 are formed to cut through soft tissue, such as the periosteum, and pierce into bone when the bone plate 68 is secured to bone. When one or more of the claws 80 pierce into bone, they, in conjunction with one or more of the bone screws 82, prevent movement of the bone plate 68 relative to the bone.

Best shown in FIGS. 3A-3D, the claws 80 are spaced inwardly of a perimeter of the side surface of the bone plate 68 on at least one side and depend downwardly from the bone pad surface 83 such that when the claws 80 are drawn into the bone 22, the bone pad surface 83 contacts the bone 22 and acts as a stop to prevent further penetration of the claws 80 into the bone 22 and improve stability. The claws 80 are angled to form a sharp point in order to pierce the bone 22. Additionally, the acute angle σ of the claws 80 relative to a vertical edge of the side surface about the perimeter of the bone plate 68 directs the sharp point away from the perimeter to protect users during handling.

In some cases, the bone pad surfaces 83 are planar and the claws 80 are spaced inwardly from the peripheral edge of the bone pad surface 83 about the entire periphery of the bone pad surface 83 so that the bone pad surface 83 is able to contact bone about the entire claw 80. In other cases, like that shown in FIG. 3B and FIG. 3C, the bone pad surface 83 extends only on certain sides of the claws 80. For instance, the claw 80 may integrally extend in a continuous fashion from the bottom surface of the bone plate 68 with bone pad surfaces 83 being defined only on either side of the claw 80 and/or between the claw and the side surface. In other cases, the bone pad surface 83 may extend on only one side of the claw 80 to act as a stop to prevent further penetration of the claw 80 into the bone once fully secure.

The claws 80, when engaged in bone, also support the bone plate 68 on the bone so that a space is provided beneath the bone plate 68 and above the surface of the bone. The bottom surface of the bone plate 68 is generally concave to define this space (see FIG. 3D). In some cases, tissue such as muscle, ligaments, and the like may be present on top of the bone to which the bone plate 68 is to be secured. This tissue can be accommodated in this space without affecting the engagement of the claws 80 in the bone.

Each of the kinematic connector assemblies 46 comprises a key 48 with kinematic elements 56, 58, 60 releasably secured in a receiver 50. In the embodiment shown in FIG. 3, the extension arm comprises a key 48 coupled to the adjustable mount 76 at the first end, and a receiver 50 affixed to the second end. The tracker head 42 comprises a receiver 50 and the bone plate 68 comprises a key 48. The key 48 at the first end of the extension arm 44 is engageable with the receiver 50 on the tracker head 42 to couple the tracker head 42 to the extension arm 44. The key 48 on the bone plate 68 is engageable with the receiver 50 at the second end of the extension arm 44 to couple the bone plate 68 to the extension arm 44.

As previously discussed, the first and second kinematic connector assemblies 46 are the same. It is to be appreciated that any key 48 is compatible with any receiver 50 such that tracker heads, extension arms, bone plates, and other accessories may be used interchangeably as needed. For example, as mentioned above, the key 48 on the bone plate 68 is engageable with the receiver 50 on the tracker head 42 to couple the bone plate 68 directly to the tracker head 42.

Furthermore, while the tracker head 42 comprises the receiver 50, the bone plate 68 comprises the key 48, and the extension arm comprises the key 48 and the receiver 50 in an exemplary embodiment, it is to be appreciated that the tracker head 42, the extension arm 44, and the bone plate 68 can comprise either of the key 48 or the receiver 50 in any combination such that various configurations of the tracker assembly 40 are possible. For example, the tracker head 42 may comprise the key 48 and the extension arm 44 may comprise the receiver 50. Alternatively, the extension arm 44 may comprise two receivers in order to prevent the tracker head 42 being coupled to the bone plate 68 and vice-versa.

Figure 4A:
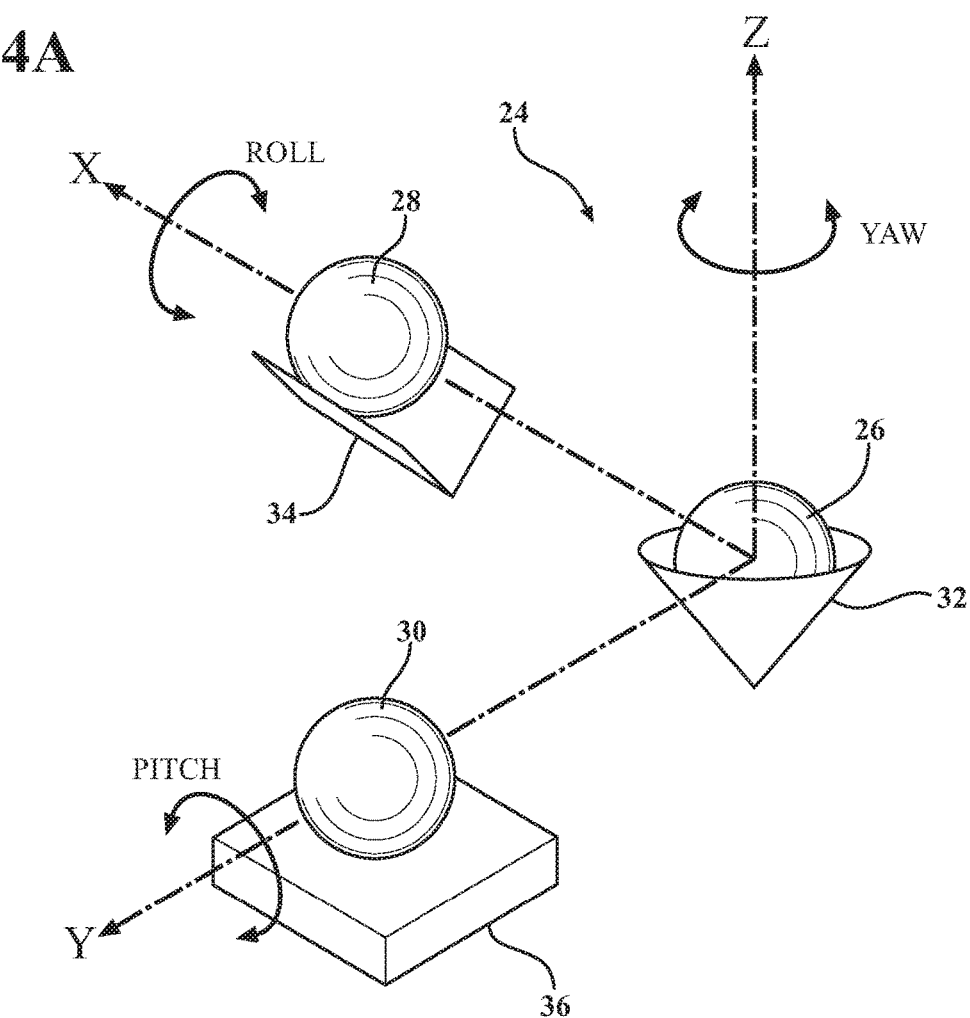
FIG. 4A is a perspective view of three translational degrees of freedom and three rotational degrees of freedom as applied to a conceptual kinematic coupler.

Typically, the object that is to be tracked is a "rigid body". As shown in FIG. 4A, rigid bodies have six degrees of freedom in 3-dimensional space; three translational degrees of freedom along axes X, Y, Z and, three rotational degrees of freedom pitch, roll, and yaw through rotation about the axes X, Y, Z. In order to control the position and orientation of the rigid body, all six degrees of freedom must be constrained. The rigid body can be constrained in one degree of freedom at one point of contact with a second rigid body. Therefore, two rigid bodies with exactly six points of contact will be constrained in all six degrees of freedom.

A conceptual kinematic coupler 24 is shown in FIG. 4A. The conceptual coupler 24 includes three spheres 26, 28, 30 each arranged along one of the axes X, Y, Z and fixed relative to one another. The conceptual coupler 24 further includes a cone receiver 32, a channel receiver 34, and a planar receiver 36 also fixed relative to each other. Each of the receivers 32, 34, 36 receives one sphere. The nature of the spheres and the receivers dictates the points of contact.

When the conceptual kinematic coupler is assembled, each receiver 32, 34, 36 contacts one of the spheres 26, 28, 30. The cone receiver 32 contacts the first sphere 26 at three points, to constrain translation along each of the axes X, Y, Z. The channel receiver 34 contacts the second sphere 28 at two points to constrain two rotational degrees of freedom, pitch and yaw. The planar receiver 36 contacts the third sphere 30 at one contact point to constrain one degree of freedom, roll. Combining all three receivers 32, 34, 36 with all three spheres 26, 28, 30 fully constrains the conceptual kinematic coupler 24 in each of the six degrees of freedom and via six contact points.

Figure 4B:
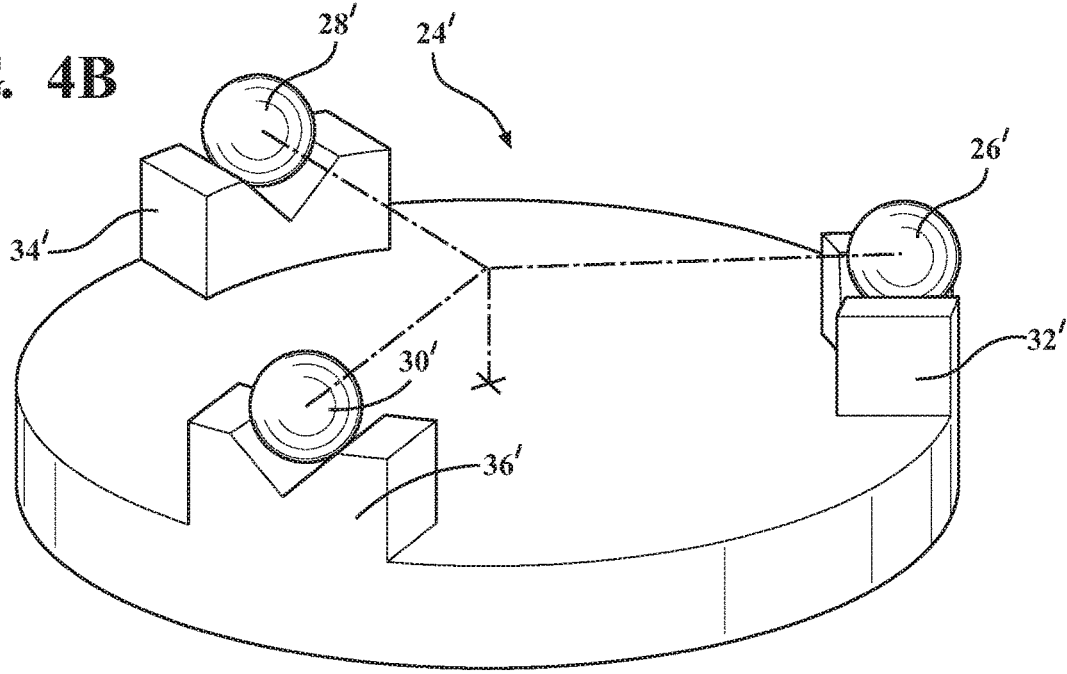
FIG. 4B is another perspective view of three translational degrees of freedom and three rotational degrees of freedom as applied to a conceptual kinematic coupler.

An alternative kinematic coupler 24' is shown in FIG. 4B, in which the receivers 32', 34', 36' are all V-groove shaped receivers for receiving the spheres 26', 28', 30'. Each of the V-groove shaped receivers contacts one of the spheres 26', 28', 30' at exactly two contact points so that all three receivers 32', 34', 36' with three spheres 26', 28', 30' fully constrains six degrees of freedom.

Figure 5:
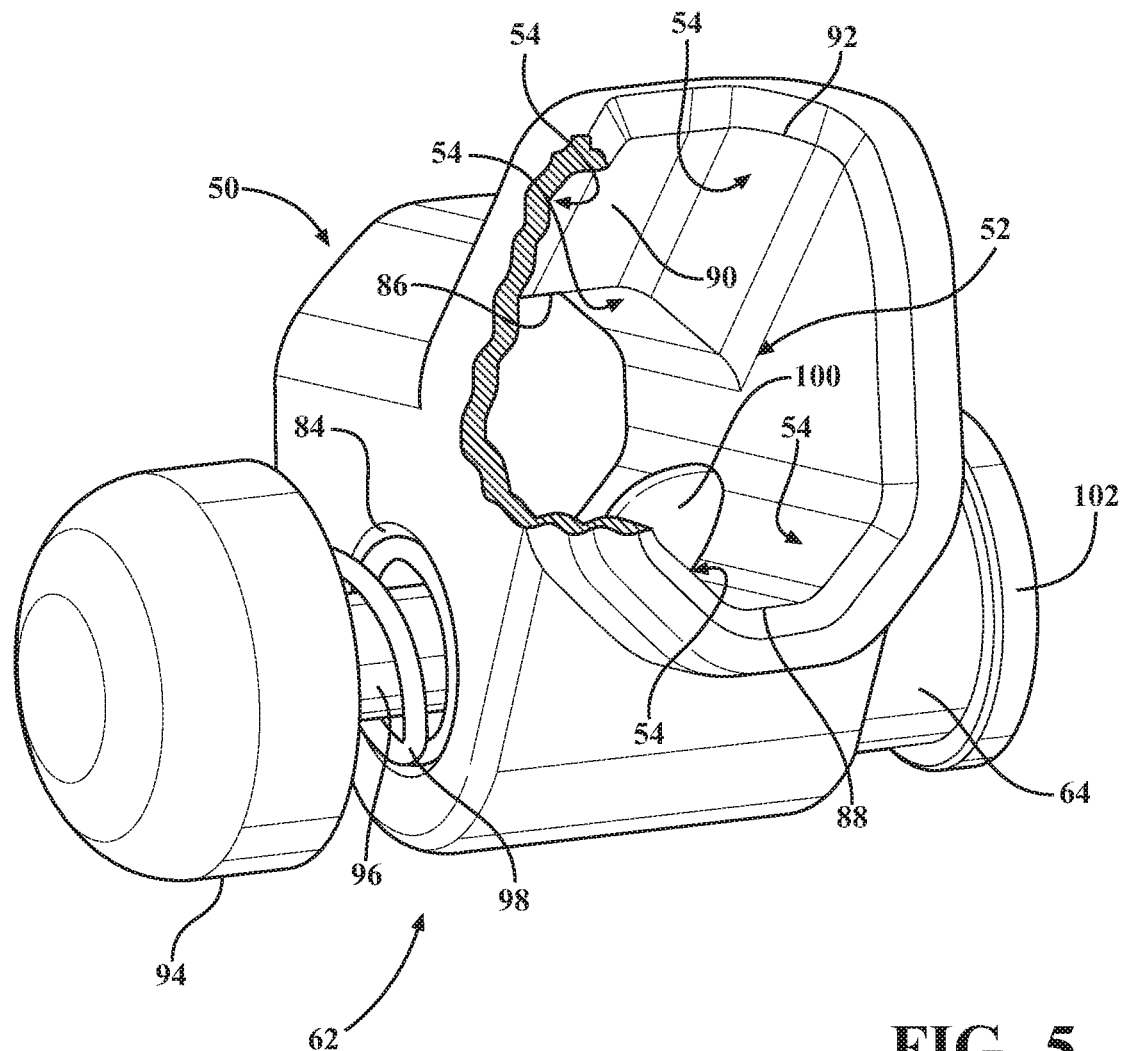
FIG. 5 is a partially cross-sectional view of a receiver of a kinematic connector assembly.
Figure 6:
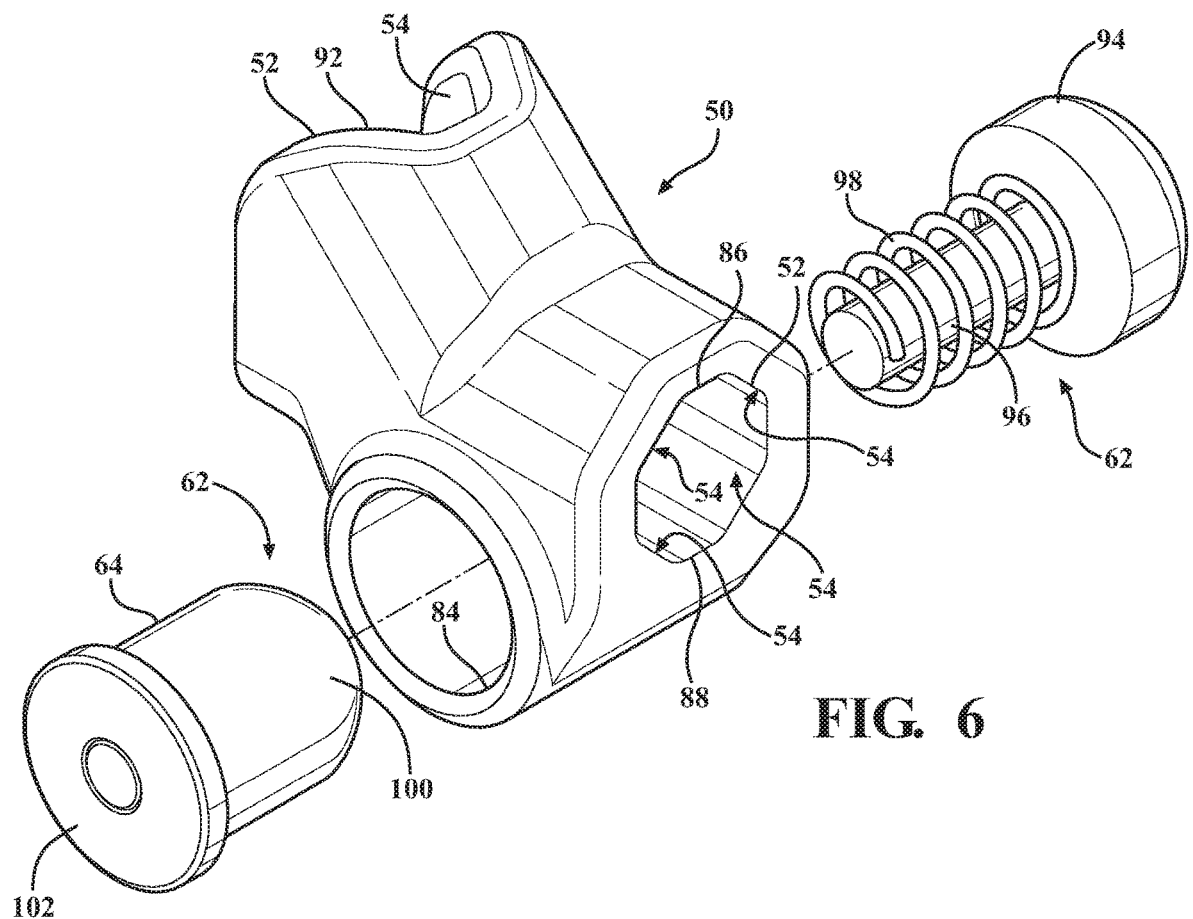
FIG. 6 is an exploded view of the receiver and a preloading mechanism of the kinematic connector assembly of FIG. 5.

Referring now to FIGS. 5 and 6 the receiver 50 of the kinematic connector assembly 46 is shown. The receiver 50 defines a cavity 52 to receive the key 48. The cavity 52 is defined at least partially by a plurality of constraint surfaces 54 accessible in the cavity 52.

The constraint surfaces 54 define three channels 86, 88, 90 to receive the key 48 in the cavity 52. A first channel 86 and a second channel 88 extend through the cavity 52 and are substantially parallel to one another. A third channel 90 intersects the first channel 86 at an angle θ (see FIG. 11B). The angle θ is approximately 120 degrees, but other angles such as 45, 60, and 240 degrees are also possible. As illustrated, the second and third channels 88, 90 terminate at a mouth portion 92 of the cavity 52. The mouth portion 92 is tapered such that the cavity 52 reduces in size further into the receiver 50.

The constraint surfaces 54 of the receiver 50 define each channel 86, 88, 90 such that at least one constraint surface 54 in each channel 86, 88, 90 contacts one of the kinematic elements 56, 58, 60 at only two points. The channels 86, 88, 90 may each be defined by two planar constraint surfaces 54. The two planar surfaces may be joined by a third surface that does not contact the kinematic elements 56, 58, 60. In the present embodiment, the channels 86, 88, 90 are substantially trapezoidal with two constraint surfaces 54 interconnected by a third non-contacting surface. The constraint surfaces 54 may also intersect such that the channels 86, 88, 90 form a V-shape. Each channel 86, 88, 90 may further define a single constraint surface, such as a curved U shape, arch shape, or other arcuate shape of which two contact points are made.

Figure 7:
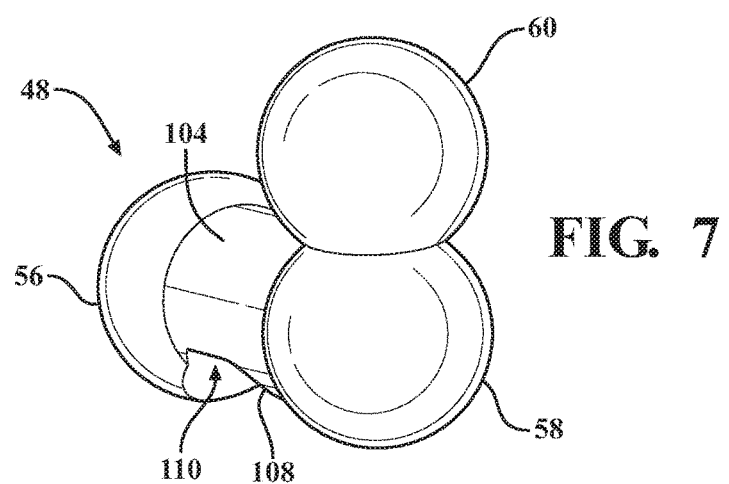
FIG. 7 is a perspective view of a key for a kinematic connector assembly.
Figure 8:
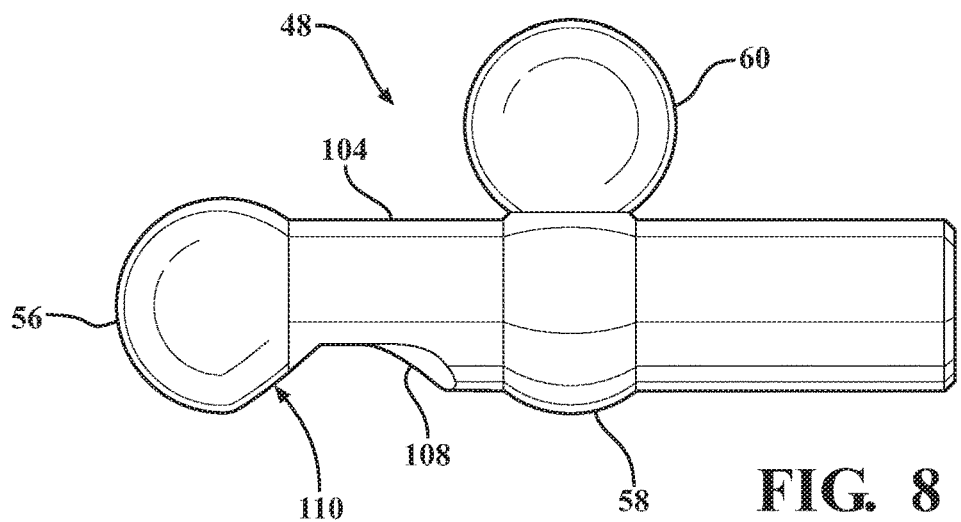
FIG. 8 is a side view of the key of FIG. 7 for a kinematic connector assembly.
Figure 9:
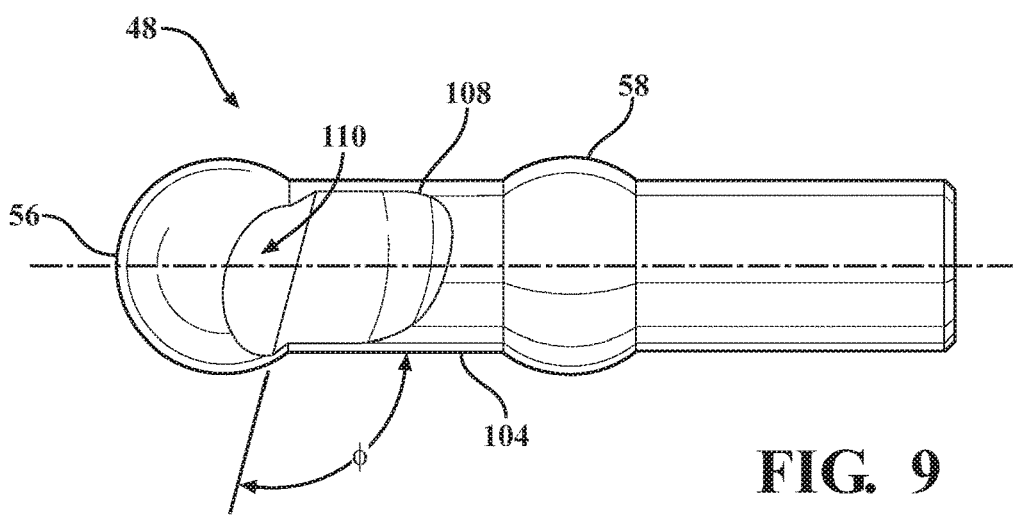
FIG. 9 is a bottom view of the key of FIG. 7 for a kinematic connector assembly.
Figure 10:
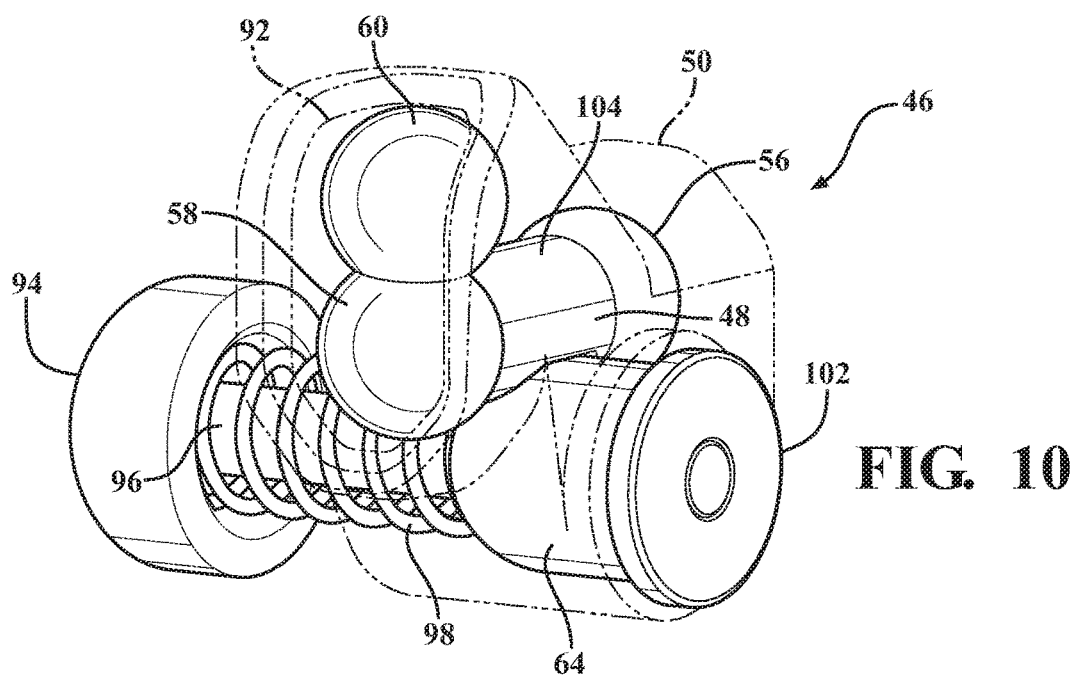
FIG. 10 is a perspective view of a kinematic connector assembly including a key and a receiver in phantom.

FIGS. 7-9 show the key 48 of the kinematic connector assembly 46. The key 48 comprises a post 104 defining a longitudinal axis. The key 48 further comprises a triplicity of the kinematic elements 56, 58, 60 each fixed to the post 104. The kinematic elements 56, 58, 60 repeatably position the key 48 in the cavity 52 of the receiver 50. The kinematic elements 56, 58, 60 contact the receiver 50 at the plurality of constraint surfaces 54 such that the key 48 is kinematically constrained to the receiver 50 by being constrained by six points of contact 66A-F with the receiver 50 (see FIGS. 11A, 11B, 12A, and 12B).

Each kinematic element 56, 58, 60 comprises a spherical segment. A distal kinematic element 56 is fixed to a distal end of the post 104. A medial kinematic element 58 is fixed to the post 104 and axially spaced from the distal kinematic element 56. A dorsal kinematic element 60 is disposed on the medial kinematic element 58 and is radially spaced from the longitudinal axis. The post 104 extends proximally beyond the medial kinematic element 58.

The dorsal kinematic element 60 includes a stem 106 (see FIG. 11B) pressed into the post 104 and further secured by welding. The distal and medial kinematic elements 56, 58 may be integrally formed with the post 104. It is additionally contemplated that the kinematic elements 56, 58, 60 may be fixed to the post 104 through several methods such as, but not limited to screw threads or integrally formed with the post 104.

Figure 11A:
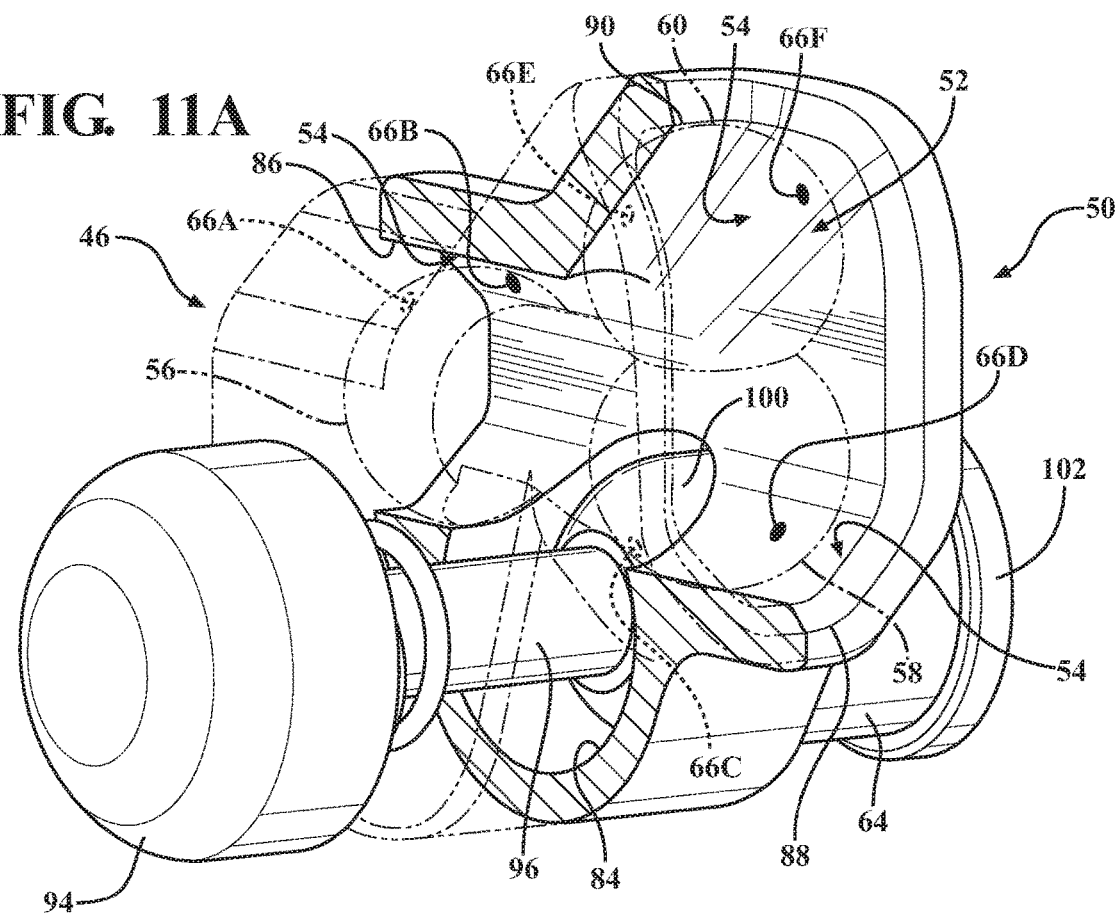
FIG. 11A is a perspective cross-sectional view of the receiver and the key in phantom of the kinematic connector assembly of FIG. 10.
Figure 12A:
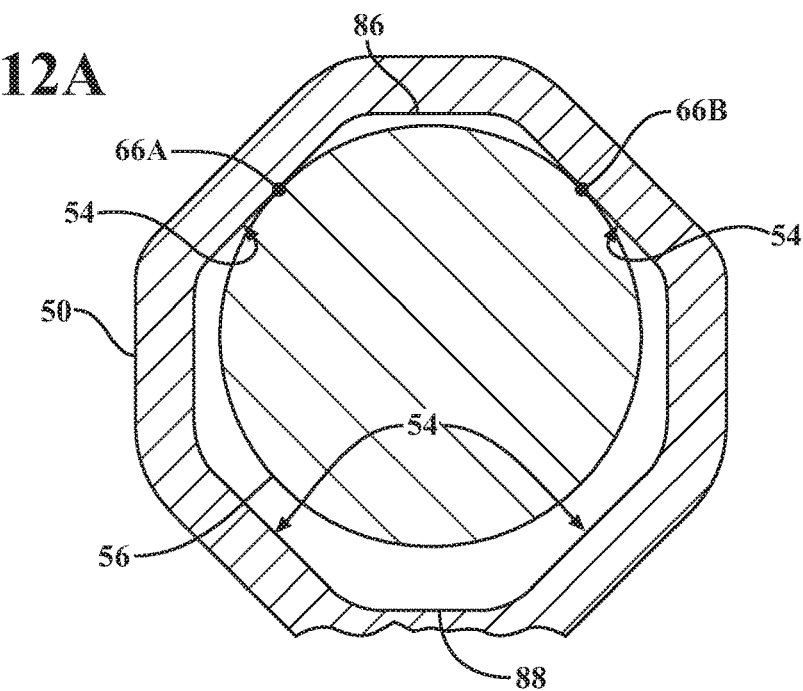
FIG. 12A is a cross-sectional view of the receiver and the key of the kinematic connector assembly of FIG. 11B taken along line 12A.
Figure 12B:
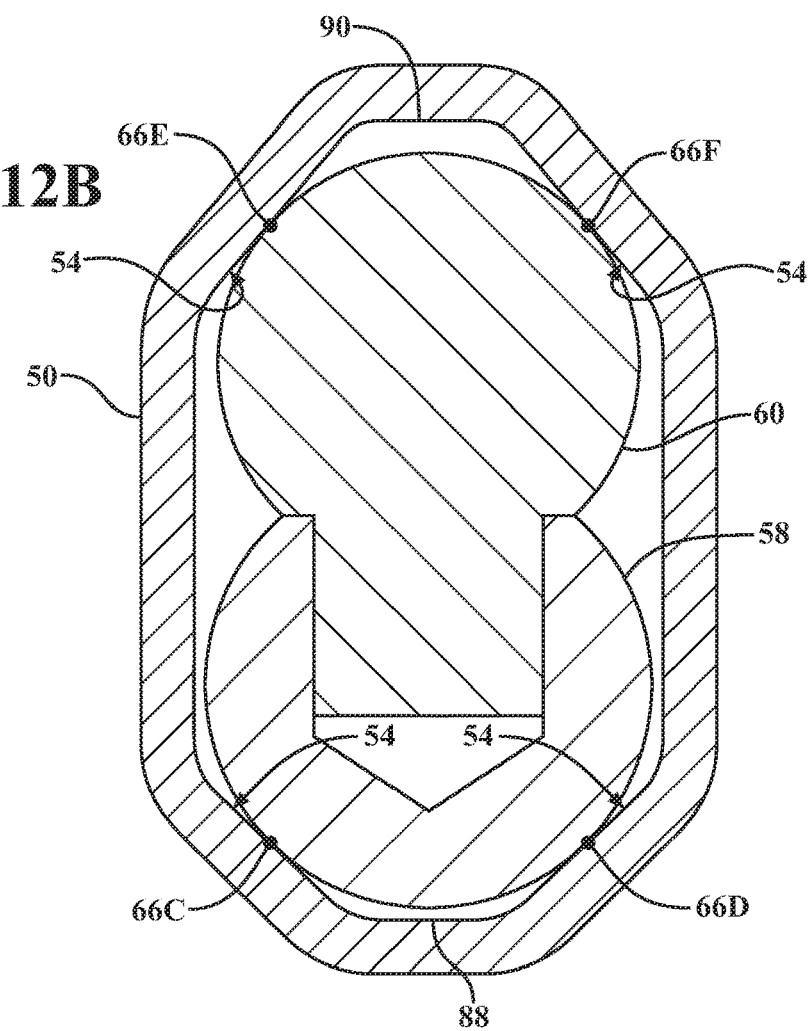
FIG. 12B is a cross-sectional view of the receiver and the key of the kinematic connector assembly of FIG. 11B taken along line 12B.

Shown in FIGS. 11A, 12A, and 12B, the six points of contact 66A-F kinematically constrain the key 48 in the receiver 50 by constraining all six degrees of freedom. Each kinematic element/channel engagement constrains two degrees of freedom, for instance, in the embodiment shown, the medial and dorsal kinematic elements 58, 60 are seated in the second and third channels 88, 90 respectively to constrain four degrees of freedom of the key 48. The distal kinematic element 56 is seated in the first channel 86 to constrain the remaining two degrees of freedom of the key 48 in the receiver 50. In other embodiments, the receiver and key can be configured such that one kinematic element constrains three degrees of freedom, another constrains two degrees of freedom, and a third constrains one degree of freedom, or other combinations are possible so long as exactly six degrees of freedom are constrained.

Because the key 48 is constrained at exactly six points of contact 66A-F in the receiver 50, the key 48 will always be coupled to the receiver 50 in the same position and orientation relative to the receiver 50. This allows the key 48 to be de-coupled from and coupled to the receiver 50 in a known position such that the connection is repeatable and deterministic.

Figure 11B:
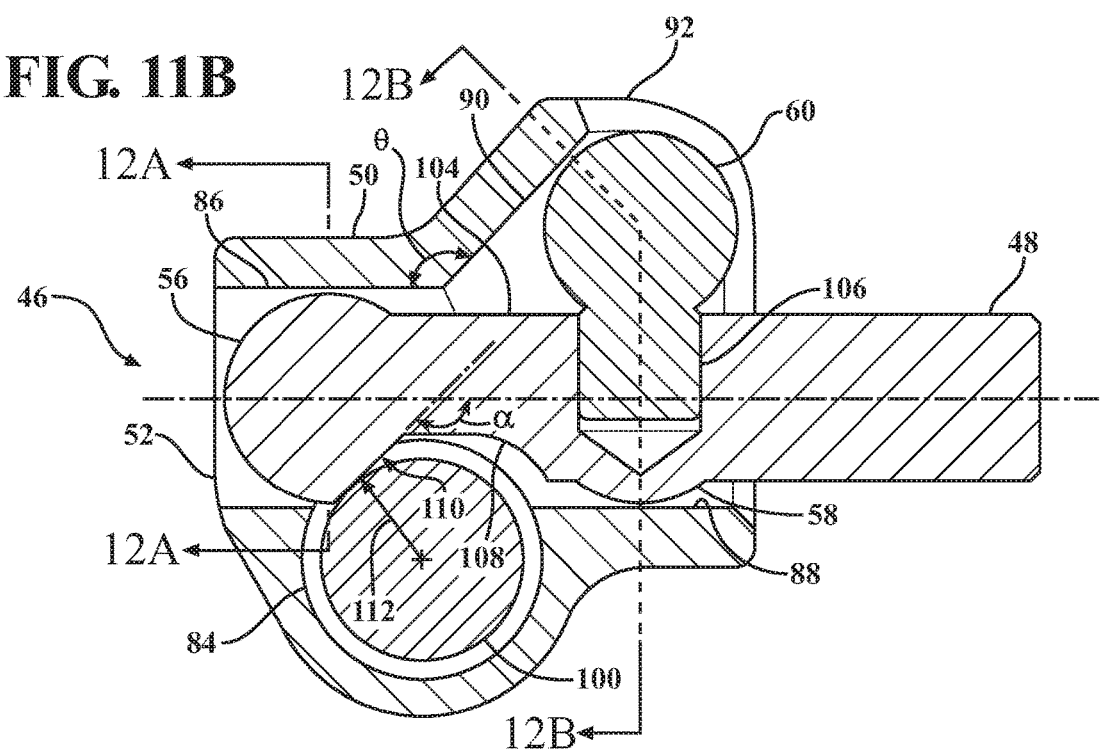
FIG. 11B is a cross-sectional view of the receiver and the key of the kinematic connector assembly of FIG. 11A.

Best shown in FIGS. 8, 9, and 11B, the post 104 further defines a clearance channel 108 in the key 48 between the distal and medial kinematic elements 56, 58. The clearance channel 108 has a loading surface 110 that is oblique to the longitudinal axis of the post 104 in two directions. The loading surface 110 is angled from the longitudinal axis at an angle Φ of greater than 90 degrees and an angle of a of greater than 90 degrees (see FIG. 11B). The loading surface 110 is generally planar and may be partially defined in the distal kinematic element 56.

As shown in FIGS. 5, 6, 13A, and 13B, the kinematic connector assembly 46 further comprises a preloading mechanism 62 to secure the key 48 in the receiver 50. The preloading mechanism 62 is configured to urge the key 48 into engagement with the receiver 50 such that the key 48 is kinematically constrained to the receiver 50 by the six points of contact 66A-F.

A preload bore 84 is defined in the receiver 50 and extends therethrough. The preload bore 84 intersects with the second channel 88 in the cavity 52. The preloading mechanism 62 comprises a load member 64 disposed in the preload bore 84. The load member 64 is coupled to one end of a shaft 96. The load member 64 is partially disposed in the preload bore 84 with the shaft 96 extending therethrough. The load member 64 is movable between a clamped position and an unclamped position to secure the key 48 in the receiver 50.

The load member 64 is substantially cylindrical with a first and second end. The load member 64 has a diameter smaller than a diameter of the preload bore 84 such that the load member 64 is slidable in the preload bore 84. The load member 64 is arranged with the first end disposed in the preload bore 84. A spherical segment 100 is formed on the first end of the load member 64. A flange 102 is formed on the second end of the load member 64. The flange 102 has a diameter larger than the diameter of the preload bore 84 to limit the travel of the load member 64 in the preload bore 84. In the embodiment shown, the load member 64 is fixed to the shaft 96. It is to be appreciated that the load member 64 is fixed to the shaft 96 through a suitable mechanism such as a press fit or screw threads. The load member 64 may simply be an integral extension of the shaft 96 in some embodiments, or other form of rigid force-applying body attached to the shaft 96 in other embodiments.

The preloading mechanism 62 further comprises a biasing device 98 disposed about the shaft 96. The biasing device 98 biases the load member 64 toward the clamped position. The biasing device 98 is disposed about the shaft 96 and arranged between the receiver 50 and a push-button 94. In an exemplary embodiment, the biasing device 98 is a spring. The spring may have a spring rate of approximately 10 to approximately 25 pounds per inch (lbs/in), and more preferably approximately 20 to approximately 25 lbs/in, although additional spring rates are further contemplated.

Figure 13A:
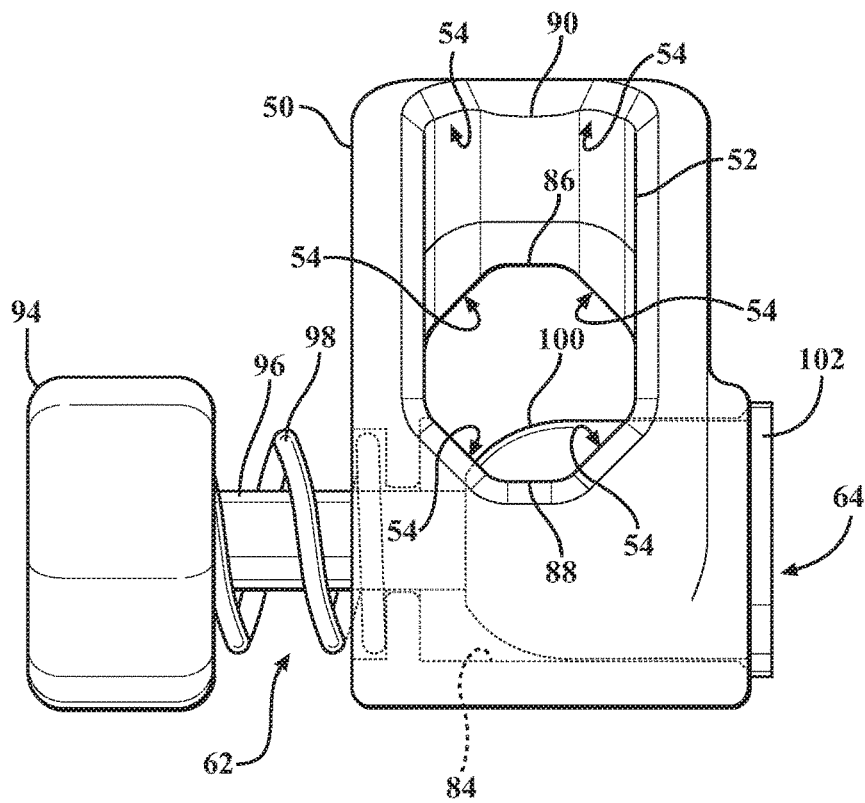
FIG. 13A is an end view of the receiver and the preloading mechanism of FIG. 5 in the clamped position.
Figure 13B:
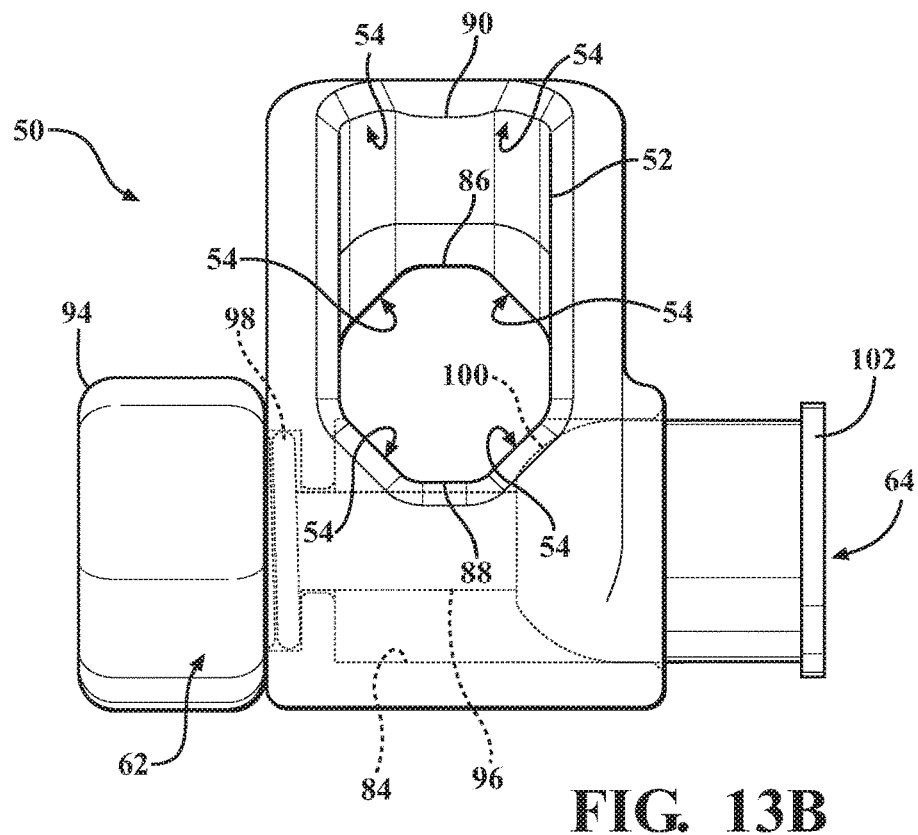
FIG. 13B is an end view of the receiver and the preloading mechanism of FIG. 5 in the unclamped position.

The load member 64 is movable relative to the receiver 50 between the unclamped position (see FIG. 13B) and the clamped position (see FIG. 13A). The push-button 94 is used to move the load member 64 toward the unclamped position from the clamped position. The load member 64 and the push-button 94 are fixed to opposite ends of the shaft 96. The push-button 94 is substantially cylindrical and defines a pocket configured to accept the biasing device 98. It is to be appreciated that the push-button 94 may be coupled to the shaft 96 through a suitable mechanism such as a press fit or screw threads.

The preloading mechanism 62 secures the key 48 in the receiver 50 so as to be fully constrained by directing each kinematic element 56, 58, 60 to contact the receiver 50 at exactly two points. As shown in FIG. 11B the distal kinematic element 56 is inserted in the cavity 52 of the receiver 50 and seated in the first channel 86. The medial and dorsal kinematic elements 58, 60 are inserted in the mouth portion 92 of the cavity 52, with the medial kinematic element 58 seated in the second channel 88 and the dorsal kinematic element 60 seated in the third channel 90.

When the key 48 is engaged with the receiver 50, the spherical segment 100 of the load member 64 contacts the loading surface 110 of the key 48. Owing to the spring force of the biasing device, a force is generated that urges the key 48 into the receiver 50. The angle Φ of the loading surface 110 allows the load member 64 to exert a force 112 (see FIG. 11B) that urges the key 48 into the receiver 50 as well as into a fully constrained position with exactly six points of contact 66A-F with the receiver 50. The spherical segment 100 can only apply force 112 perpendicular to the loading surface 110. Because the spherical segment 100 of the load member 64 acts against the planar loading surface 110, the key 48 does not become over constrained in the receiver 50. The angle Φ is also such that the kinematic connector assembly 46 is not back-drivable. For example, a pull-out force on the key 48 increases frictional force on the loading surface 110 preventing the load member 64 from moving to the unclamped position.

Figure 14:
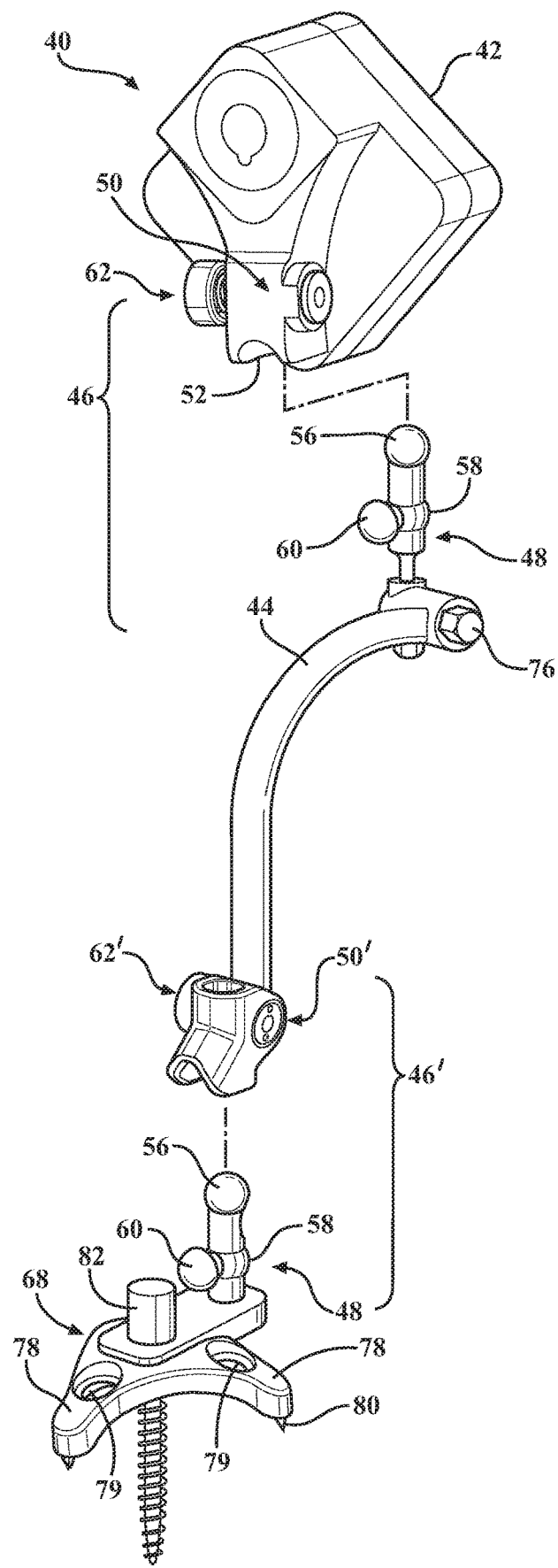
FIG. 14 is an exploded view of another embodiment of a tracker assembly.

An alternative embodiment of a preloading mechanism 62' is shown attached to the second end of the extension arm 44 in FIG. 14, and in FIGS. 15A-16C. The preloading mechanism 62' comprises a load member 64' disposed in the preload bore 84. The load member 64' is coupled to one end of a shaft 96'. The load member 64' is disposed in the preload bore 84 with the shaft 96' extending therethrough. The load member 64' is coupled to the shaft 96' with screw threads. The load member 64' is movable between a clamped position and an unclamped position to secure the key 48 in the receiver 50'. The load member 64' is substantially cylindrical with a first and second end. A spherical segment 100' (shown as a hemi-spherical element) is formed on the first end of the load member 64'. The second end of the load member 64' comprises a flat surface 69' defining a pair of pin holes 65. The pin holes 65 are used to tighten the load member 64' onto the shaft 96'.

Figure 15A:
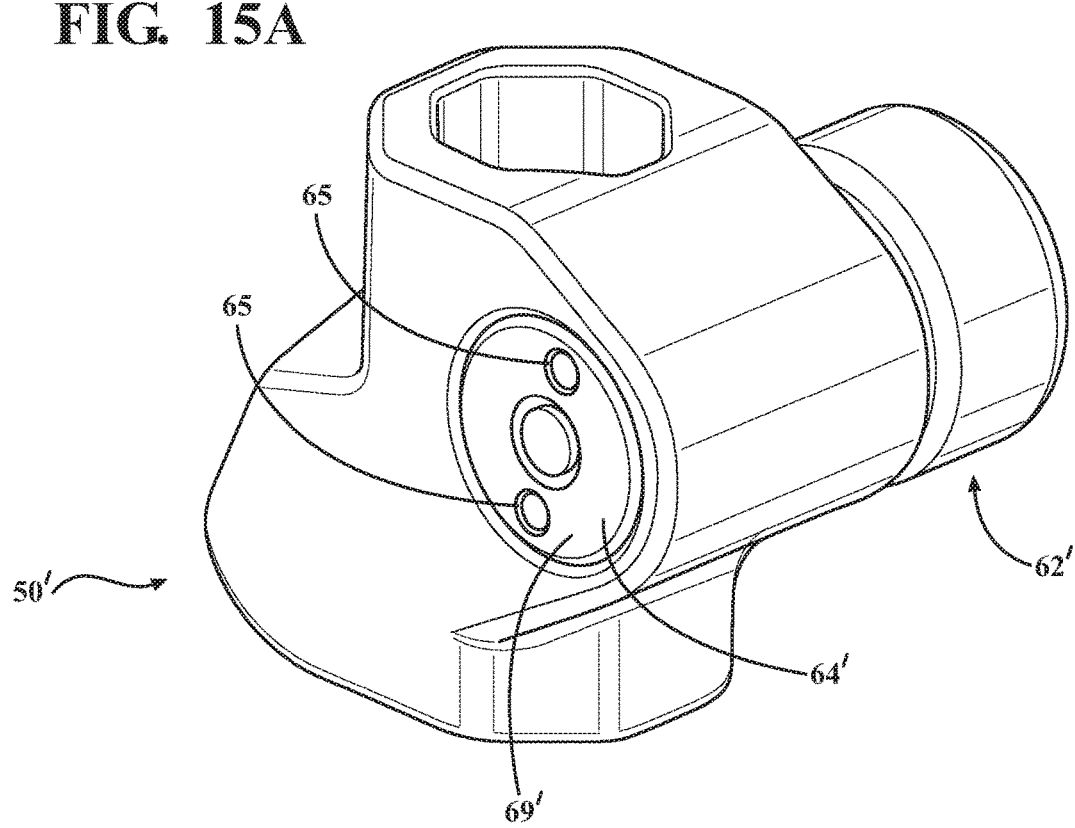
FIGS. 15A and 15B are perspective views illustrating an alternative receiver and an alternative preloading mechanism in unclamped and clamped positions.
Figure 15B:
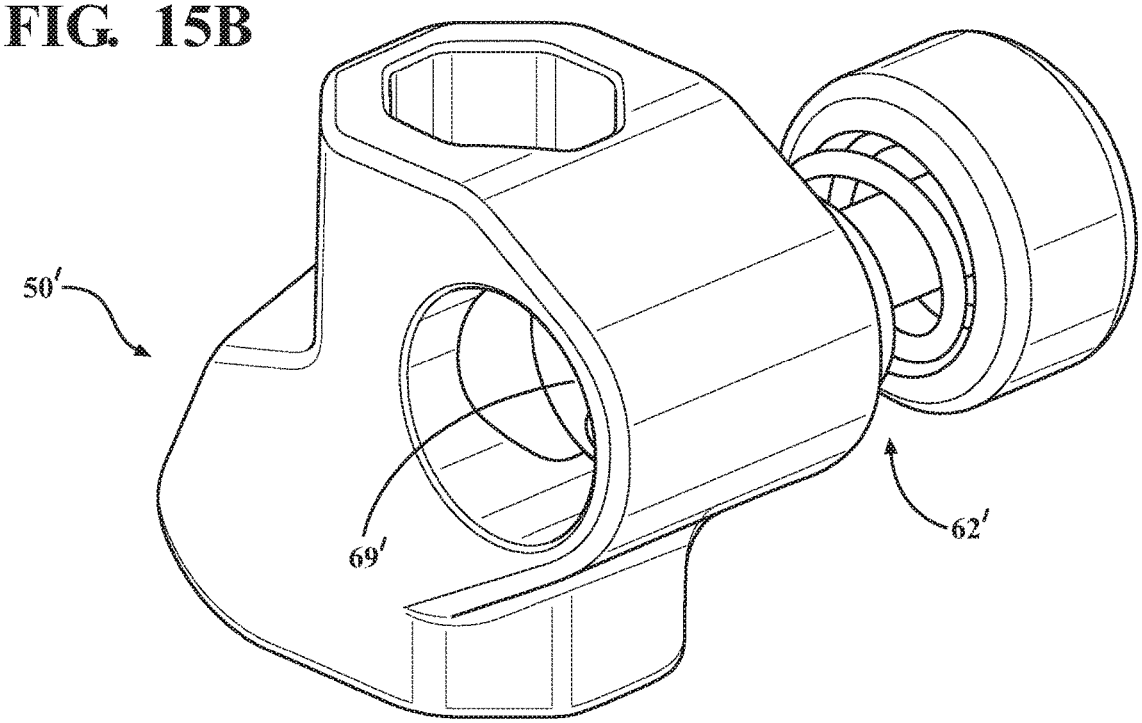
Figure 16A:
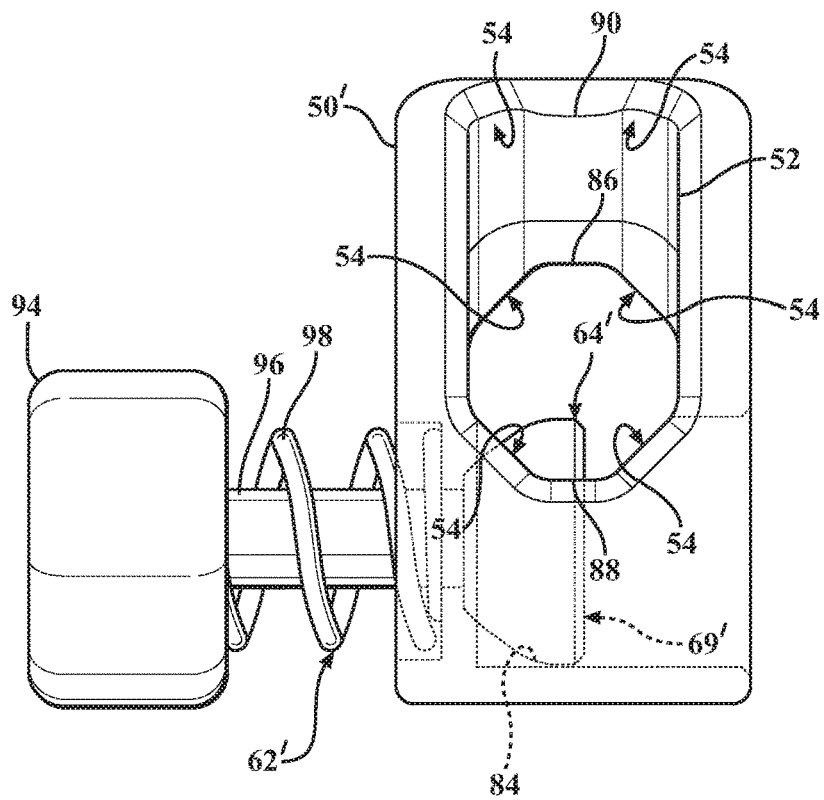
FIGS. 16A and 16B are end views illustrating the alternative receiver and the alternative preloading mechanism of FIGS. 15A and 15B in unclamped and clamped positions.
Figure 16B:
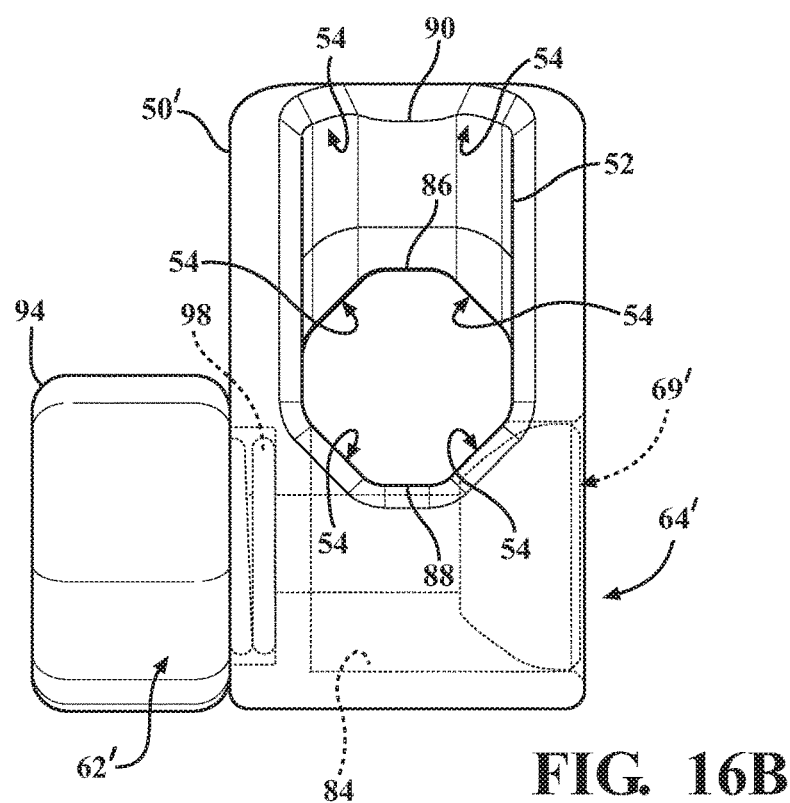
Figure 16C:
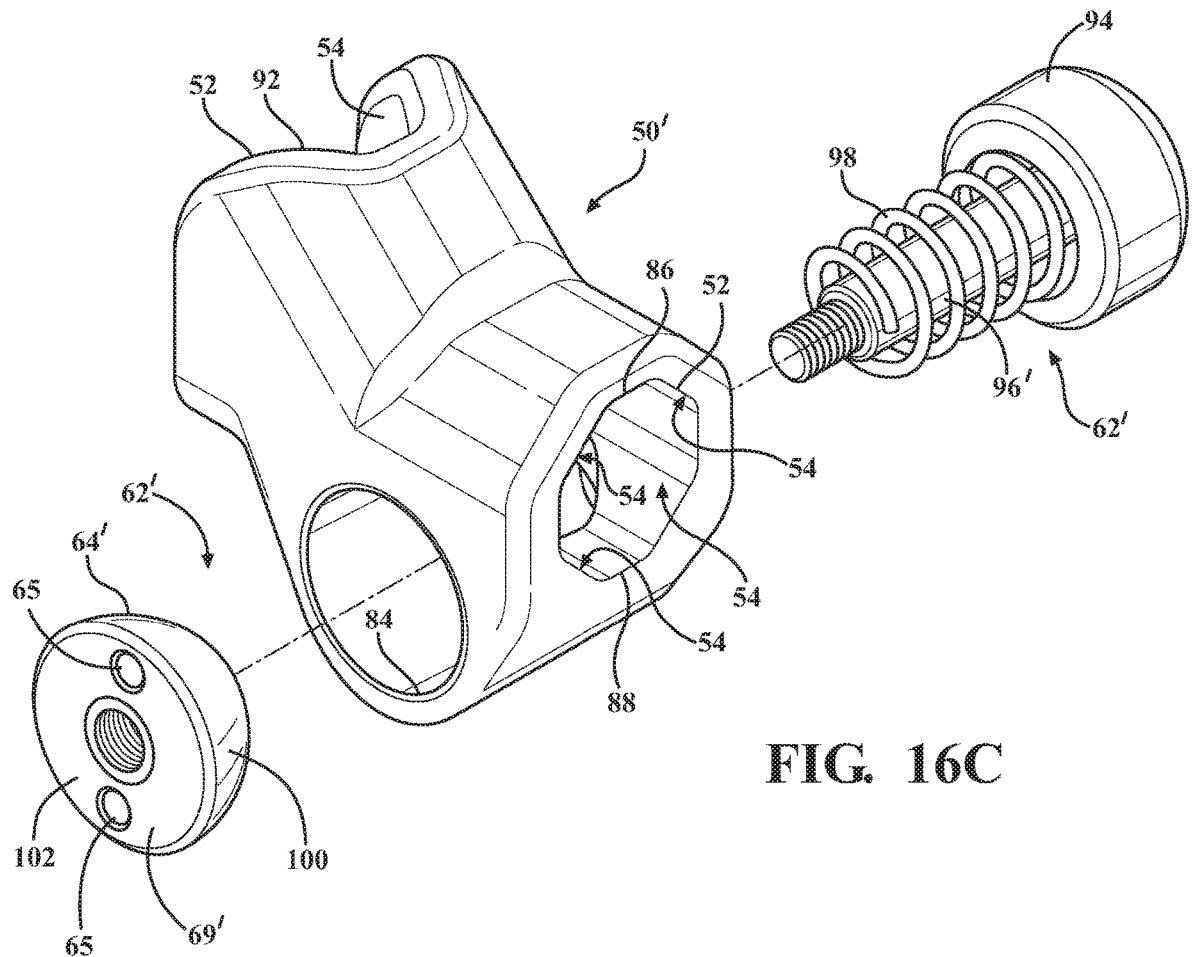
FIG. 16C is an exploded view of the alternative receiver and the alternative preloading mechanism of FIGS. 15A-16B
Figure 17A:
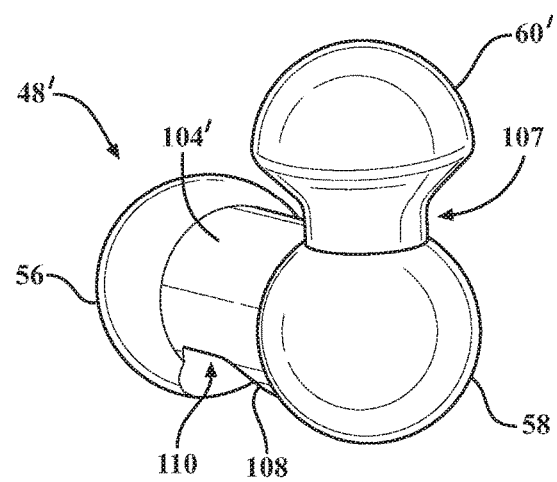
FIG. 17A is a perspective view of an alternative key for an alternative kinematic connector assembly.
Figure 17B:
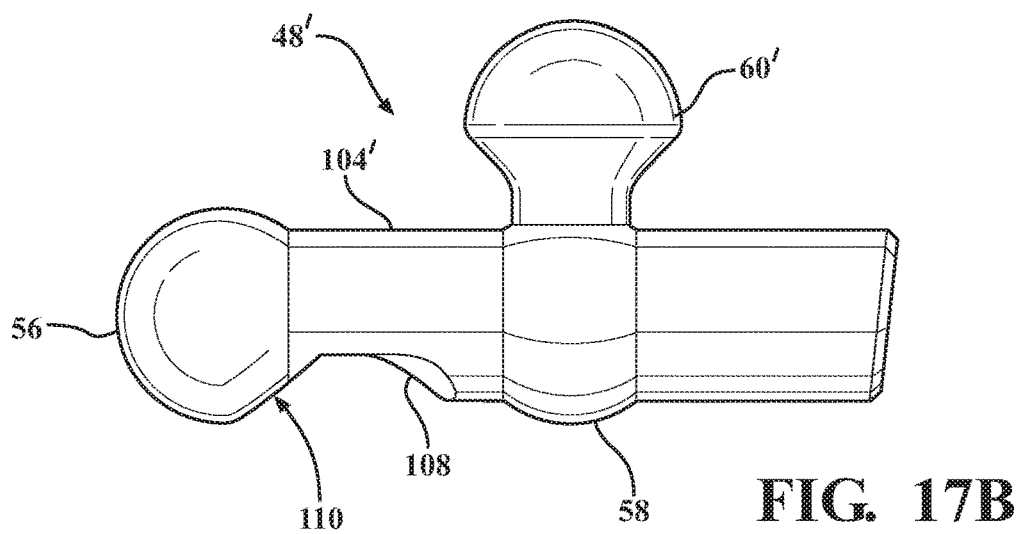
FIG. 17B is a side view of the alternative key of FIG. 17A.
Figure 18:
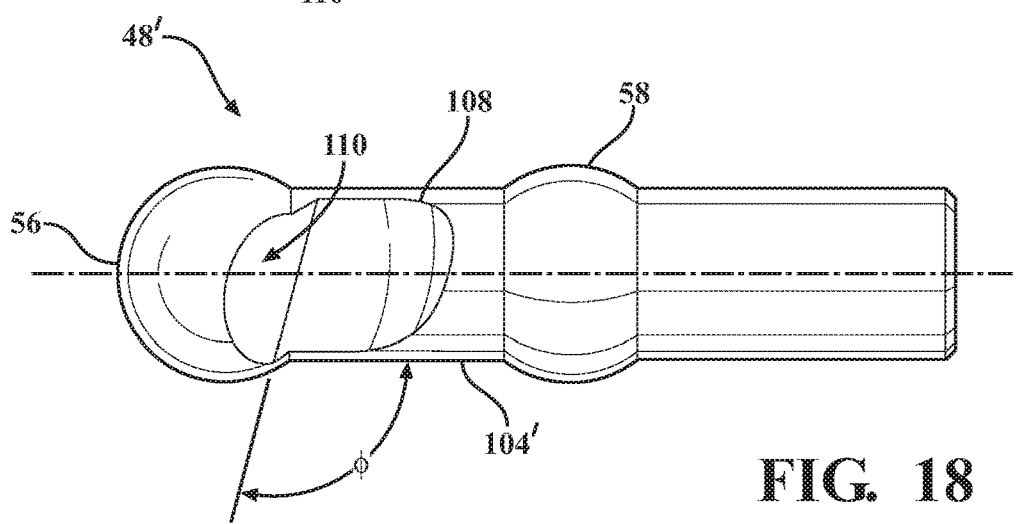
FIG. 18 is a bottom view of the key of FIG. 17A.
Figure 19:
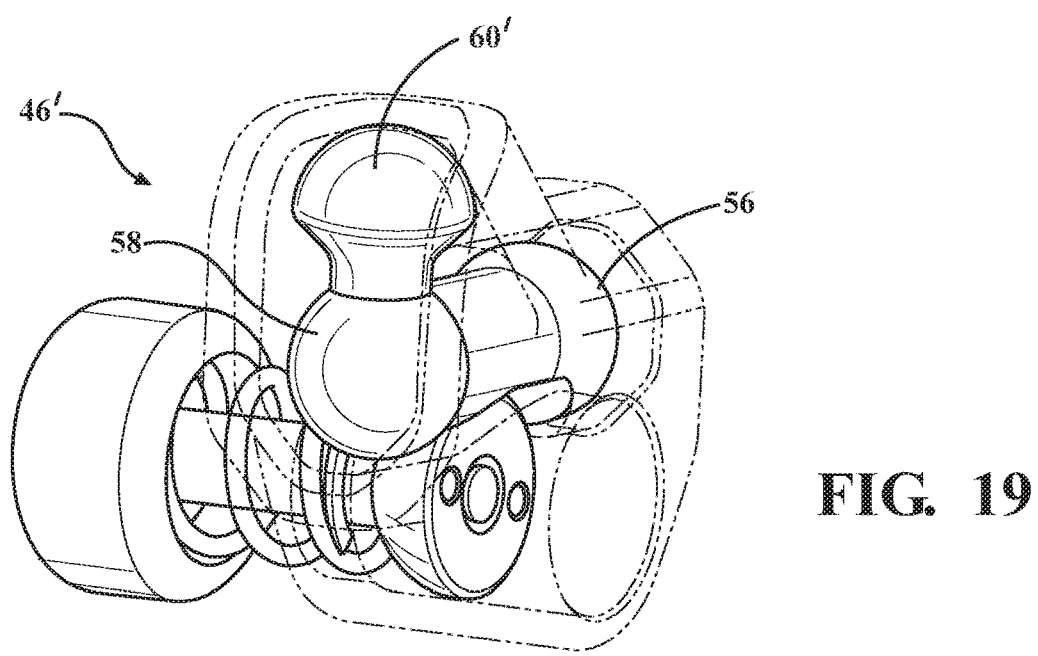
FIG. 19 is a perspective view of the alternative kinematic connector assembly including the alternative key and the alternative receiver.
Figure 20:
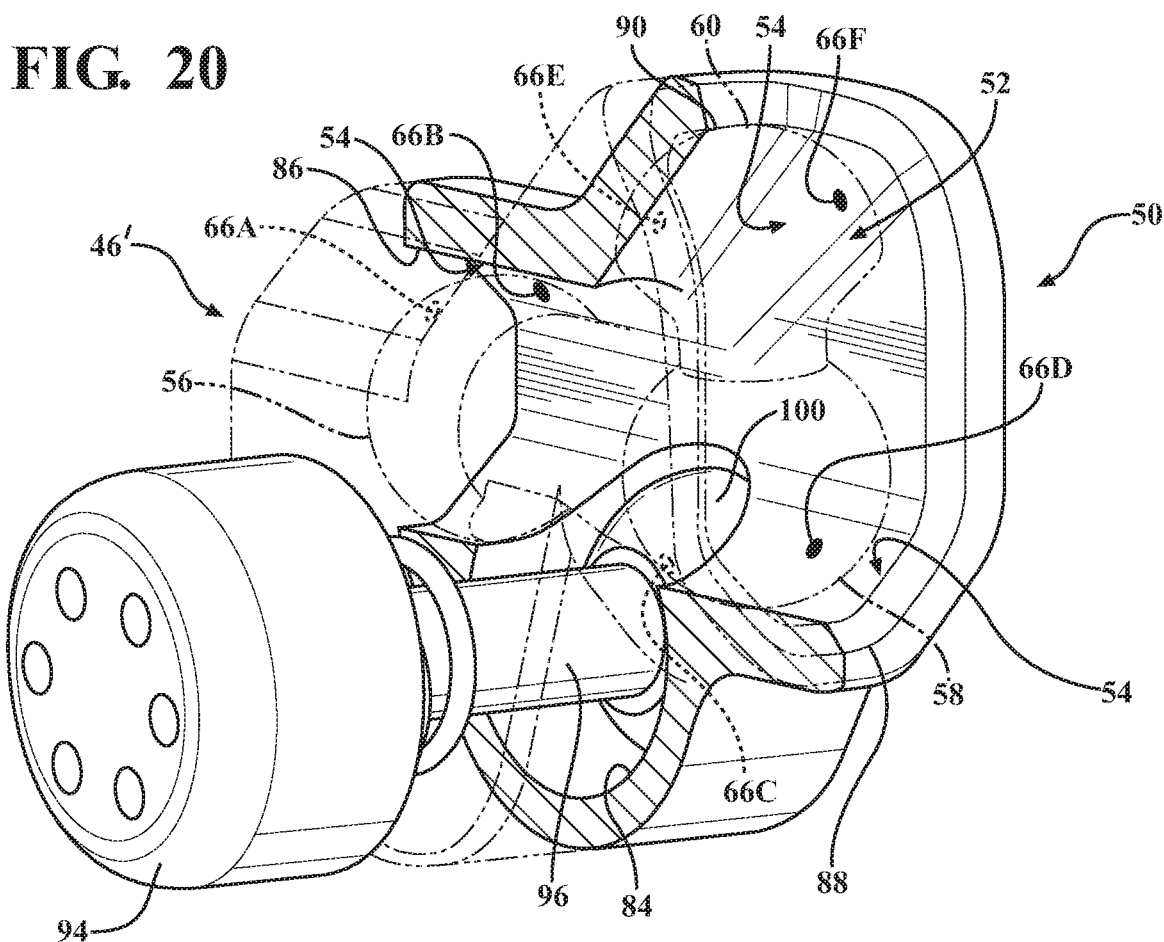
FIG. 20 is a perspective cross-sectional view of the alternative receiver and the alternative key.
Figure 21:
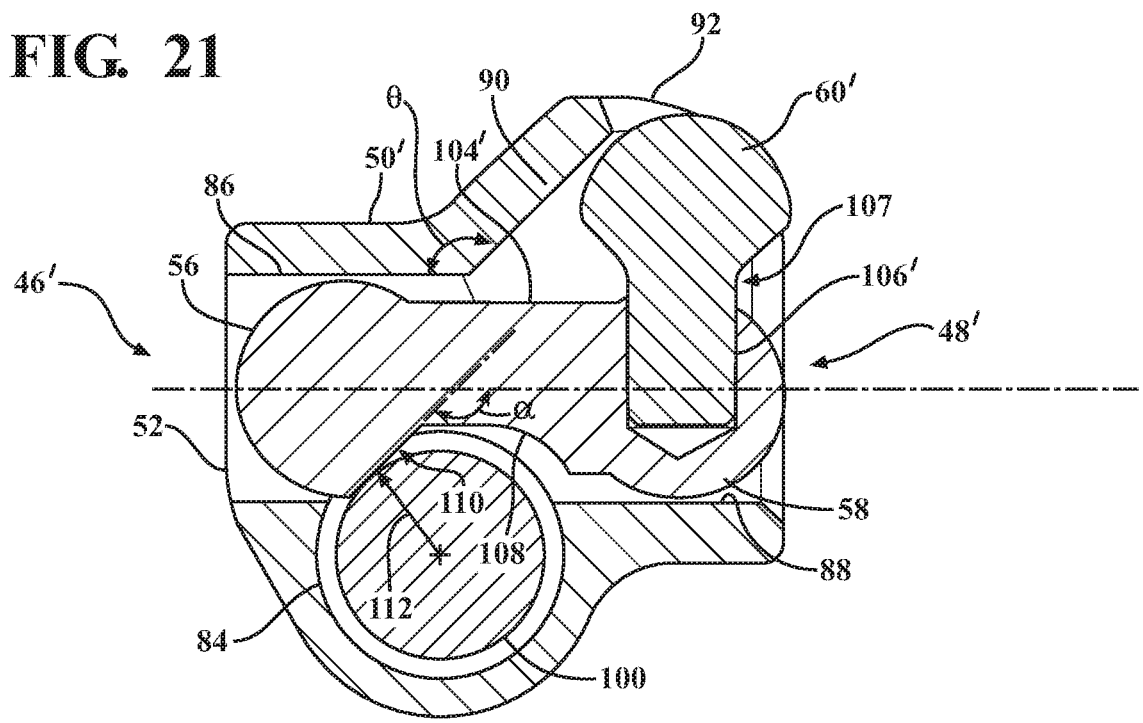
FIG. 21 is a cross-sectional view of the alternative receiver and the alternative key.

Referring to FIGS. 14, 15A, and 16B, in this embodiment, when the load member 64' is moved to the unclamped position, the second end, i.e., the flat surface 69' is substantially flush with an outer surface of the receiver 50'. As a result, the second end does not interfere with a user's grasp of the receiver 50' during use.

In FIGS. 17A-21 one alternative embodiment of the key 48' of the kinematic connector assembly 46' is shown. The key 48' comprises a post 104' defining a longitudinal axis. The key 48' further comprises a triplicity of the kinematic elements 56, 58, 60' each fixed to the post 104.

The dorsal kinematic element 60' includes a stem 106' (see FIG. 21) pressed into the post 104' and further secured by welding. The stem 106' comprises an undercut section 107 near the post 104'. The undercut section 107 allows the key 48' to be cleaned more easily.

Figures 22A, 22B:
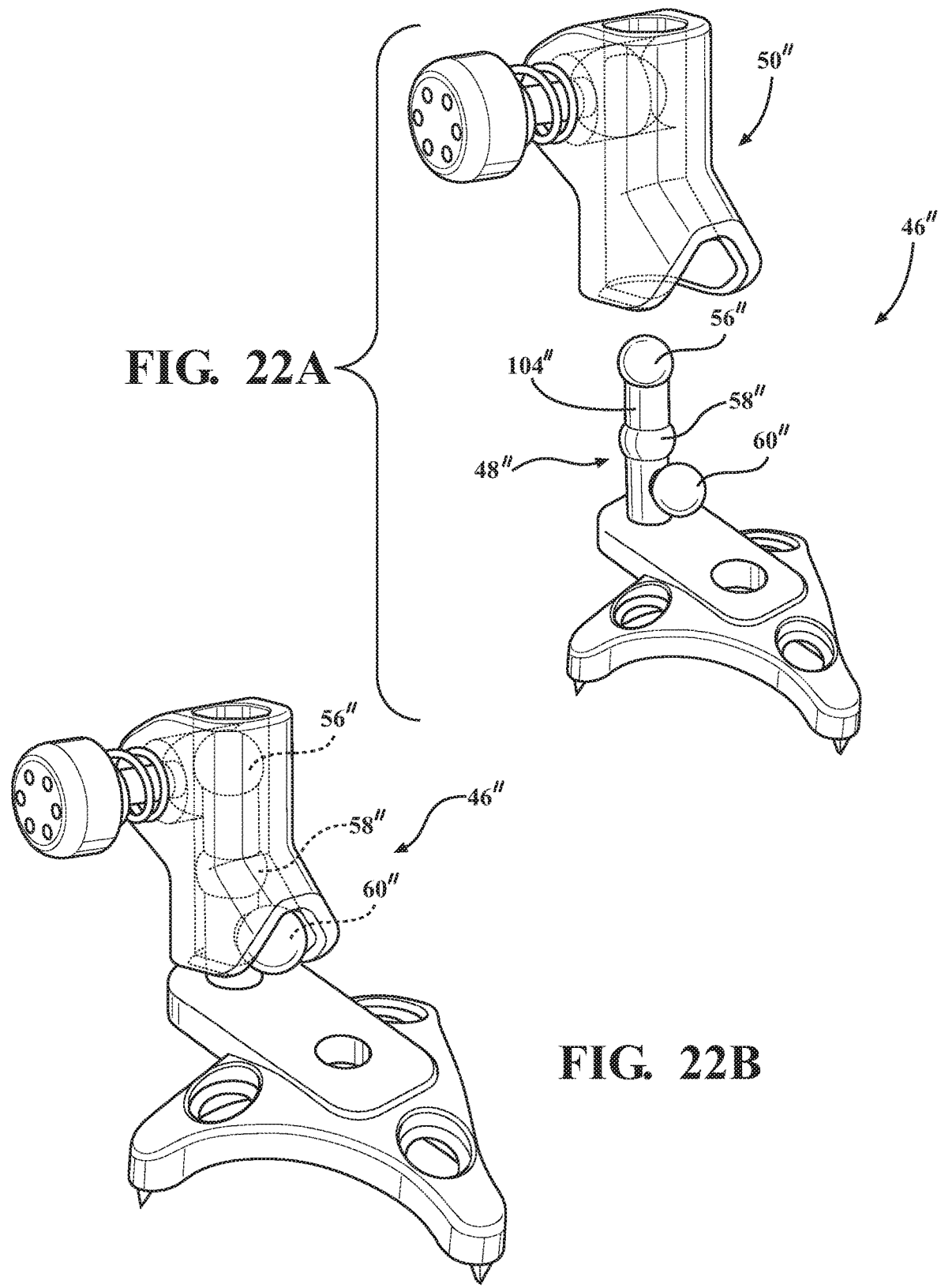
FIGS. 22A and 22B are perspective views of yet another alternative kinematic connector assembly.

In another embodiment of a key 48" shown in FIGS. 22A and 22B, the post 104" may be longer than shown in prior embodiments. The receiver 50" is proportionately longer in order to accommodate the key 48". Increased length of the key 48" increases stability of the kinematic connector assembly 46".

Figure 23A:
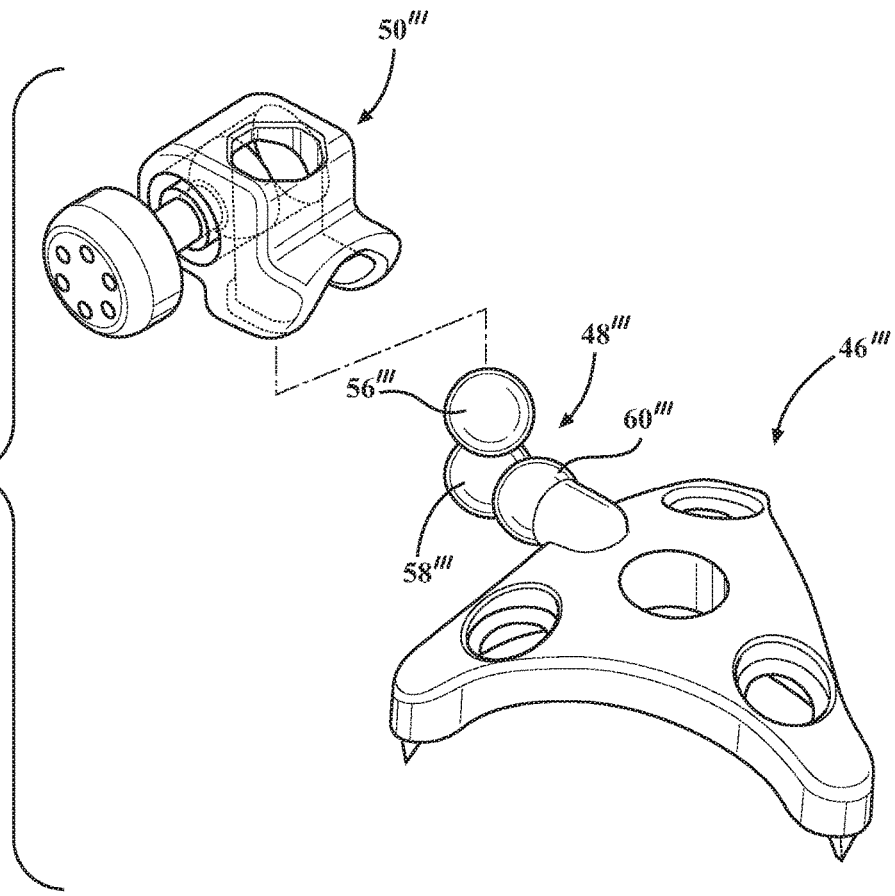
FIGS. 23A and 23B are perspective views of yet another alternative kinematic connector assembly.
Figure 23B:
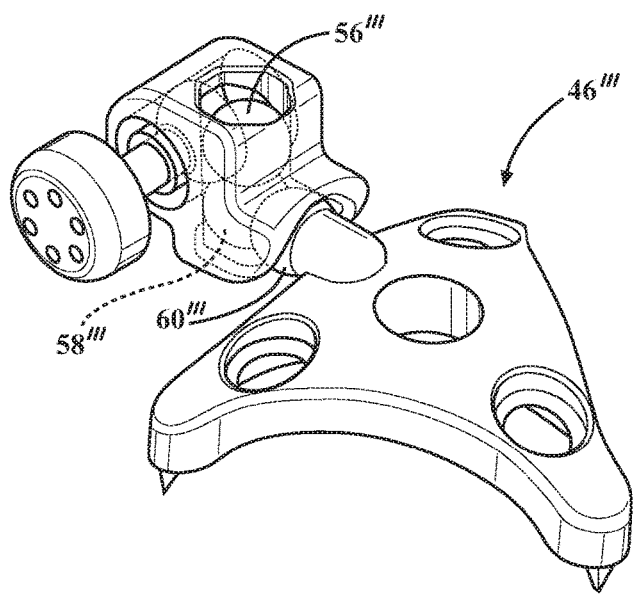
Figure 24:
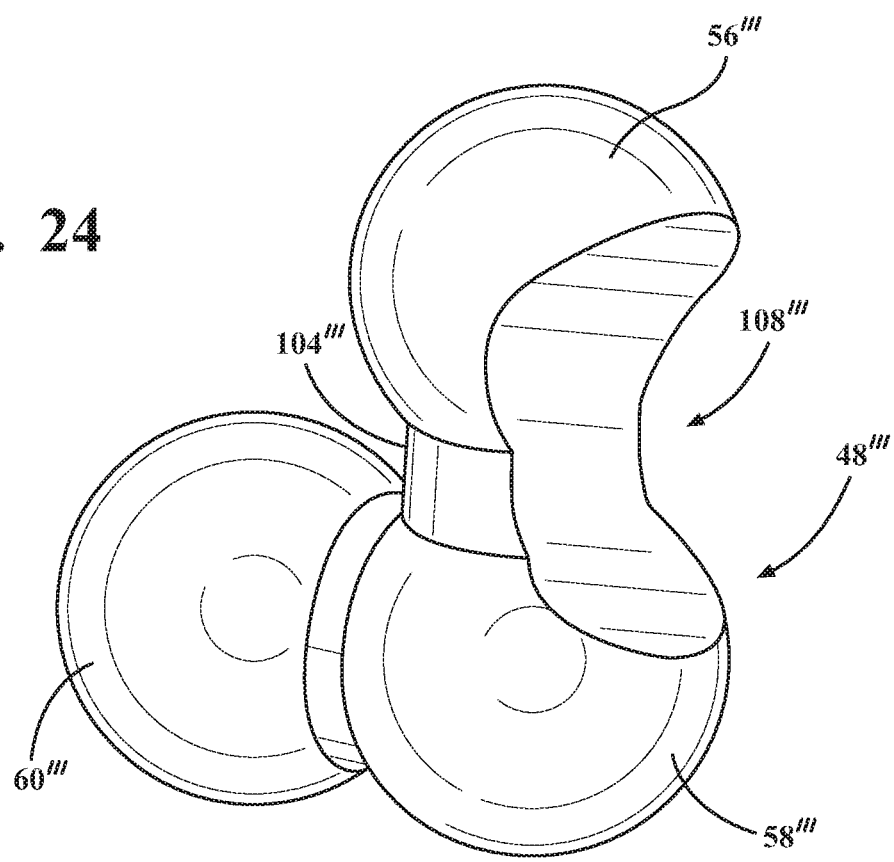
FIG. 24 is a perspective view of yet another alternative key used in the alternative kinematic connector assembly of FIGS. 23A and 23B.

In another embodiment of a key 48''' shown in FIGS. 23A-24, the post 104''' (see FIG. 24) may be shorter than shown in prior embodiments. The receiver 50''' is proportionately shorter in order to accommodate the key 48'''. Decreased length of the key 48''' allows the kinematic connector assembly 46''' to be used in more confined spaces and reduces weight. The clearance channel 108''' is similarly sized, as such the clearance channel 108''' may extend through both the distal and medial kinematic elements 56''', 58'''.

It should be appreciated that the kinematic connector assembly described herein may be used for connecting together other surgical components such as guides for powered instruments or hand tools, or for use in other industries e.g. optics, motion capture, robotics, etc.

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A kinematic connector assembly, said kinematic connector assembly comprising:
    a receiver defining a cavity and having a plurality of constraint surfaces accessible in said cavity;
    a key having a triplicity of kinematic elements to repeatably position said key in said receiver; and
    a preloading mechanism operably attached to said receiver and having a load member, said load member disposed in said receiver and arranged to secure said key in said receiver such that said kinematic elements contact said receiver at said plurality of constraint surfaces whereby said key is kinematically constrained to said receiver by being constrained by six points of contact with said receiver.

2. The kinematic connector assembly of claim 1, wherein said kinematic elements comprise spherical segments.

3. The kinematic connector assembly of claim 1, wherein said plurality of constraint surfaces define three channels.

4. The kinematic connector assembly of claim 3, wherein each of said channels are defined by two planar surfaces.

5. The kinematic connector assembly of claim 3, wherein each of said channels are defined by a curved surface arranged to contact one of said kinematic elements at only two points.

6. The kinematic connector assembly of claim 3, wherein said channels are each defined by two planar surfaces intersecting to form a V shape.

7. The kinematic connector assembly of claim 3, wherein two of said channels are parallel.

8. The kinematic connector assembly of claim 3, wherein two of said channels intersect.

9. The kinematic connector assembly of claim 1, wherein said load member is movable between a clamped position and an unclamped position and said preloading mechanism is configured to urge said key into engagement with said receiver such that said key is kinematically constrained to said receiver.

10. The kinematic connector assembly of claim 9, wherein said preloading mechanism further comprises a push-button to move said load member from said clamped position to said unclamped position.

11. The kinematic connector assembly of claim 10, wherein said preloading mechanism further comprises a shaft disposed between said load member and said push-button.

12. The kinematic connector assembly of claim 9, wherein said preloading mechanism further comprises a biasing device arranged to bias said load member toward said clamped position.

13. The kinematic connector assembly of claim 12, wherein said biasing device is a spring.

14. The kinematic connector assembly of claim 13, wherein said spring has a spring rate between 10 pounds per inch and 25 pounds per inch.

15. The kinematic connector assembly of claim 1, wherein said load member comprises a spherical segment.

16. The kinematic connector assembly of claim 1, wherein said key comprises a post defining a longitudinal axis with at least two of said kinematic elements fixed to said post.

17. The kinematic connector assembly of claim 16, wherein said key defines a loading surface oblique to said longitudinal axis of said post.

18. The kinematic connector assembly of claim 17, wherein said loading surface is planar and said load member comprises a spherical segment configured to contact said loading surface.

19. A tracker assembly to track an object, said tracker assembly comprising:
a tracker head; and
wherein said receiver of said kinematic connector assembly of claim 1 is coupled to said tracker head; or
wherein said key of said kinematic connector assembly of claim 1 is coupled to said tracker head.

20. A kinematic connector assembly comprising:
a receiver defining a cavity and having a plurality of constraint surfaces defining three channels and accessible in said cavity, wherein two of said channels are parallel;
a key having a triplicity of kinematic elements to repeatably position said key in said receiver; and
a preloading mechanism having a load member arranged to secure said key in said receiver such that said kinematic elements contact said receiver at said plurality of constraint surfaces whereby said key is kinematically constrained to said receiver by being constrained by six points of contact with said receiver.

21. A kinematic connector assembly comprising:
a receiver defining a cavity and having a plurality of constraint surfaces accessible in said cavity;
a key having a triplicity of kinematic elements to repeatably position said key in said receiver; and
a preloading mechanism comprising:
a load member movable between a clamped position and an unclamped position and arranged to secure said key in said receiver such that said kinematic elements contact said receiver at said plurality of constraint surfaces; and
a push-button configured to move said load member from said clamped position to said unclamped position;
wherein said preloading mechanism is configured to urge said key into engagement with said receiver such that said key is kinematically constrained to said receiver by being constrained by six points of contact with said receiver.

22. The kinematic connector assembly of claim 21, wherein said preloading mechanism further comprises a shaft disposed between said load member and said push-button.

23. The kinematic connector assembly of claim 21, wherein said preloading mechanism further comprises a biasing device arranged to bias said load member toward said clamped position.

24. The kinematic connector assembly of claim 23, wherein said biasing device is a spring.

25. A kinematic connector assembly comprising:
a receiver defining a cavity and having a plurality of constraint surfaces accessible in said cavity;
a key having a triplicity of kinematic elements to repeatably position said key in said receiver; and
a preloading mechanism comprising a load member having a spherical segment arranged to secure said key in said receiver such that said kinematic elements contact said receiver at said plurality of constraint surfaces whereby said key is kinematically constrained to said receiver by being constrained by six points of contact with said receiver.

26. The kinematic connector assembly of claim 25, wherein said load member is movable between a clamped position and an unclamped position and said preloading mechanism is configured to urge said key into engagement with said receiver such that said key is kinematically constrained to said receiver.

27. The kinematic connector assembly of claim 25, wherein said preloading mechanism is operably attached to said receiver and said load member is disposed in said receiver.

28. The kinematic connector assembly of claim 25, wherein said key comprises a post defining a longitudinal axis with at least two of said kinematic elements fixed to said post.

29. The kinematic connector assembly of claim 28, wherein said key defines a loading surface oblique to said longitudinal axis of said post.

30. The kinematic connector assembly of claim 29, wherein said loading surface is planar and said load member comprises a spherical segment configured to contact said loading surface.

31. A kinematic connector assembly comprising:
a receiver defining a cavity and having a plurality of constraint surfaces accessible in said cavity;
a key comprising a post defining a longitudinal axis and a triplicity of kinematic elements to repeatably position said key in said receiver, at least two of said kinematic elements fixed to said post; and
a preloading mechanism having a load member arranged to secure said key in said receiver such that said kinematic elements contact said receiver at said plurality of constraint surfaces whereby said key is kinematically constrained to said receiver by being constrained by six points of contact with said receiver.

32. The kinematic connector assembly of claim 31, wherein said preloading mechanism is operably attached to said receiver and said load member is disposed in said receiver and movable between a clamped position and an unclamped position and said preloading mechanism is configured to urge said key into engagement with said receiver such that said key is kinematically constrained to said receiver.

33. The kinematic connector assembly of claim 31, wherein said key defines a loading surface oblique to said longitudinal axis of said post.

34. The kinematic connector assembly of claim 33, wherein said loading surface is planar and said load member comprises a spherical segment configured to contact said loading surface.

* * * * *